(12) United States Patent
Min

(10) Patent No.: US 9,293,818 B2
(45) Date of Patent: Mar. 22, 2016

(54) INTRA-PERICARDIAL MEDICAL DEVICE

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 58 days.

(21) Appl. No.: 13/229,548

(22) Filed: Sep. 9, 2011

(65) Prior Publication Data

US 2013/0066399 A1 Mar. 14, 2013

(51) Int. Cl.
*A61N 1/362* (2006.01)
*A61N 1/05* (2006.01)
*H01Q 1/44* (2006.01)
*H01Q 1/22* (2006.01)
*A61N 1/372* (2006.01)
*A61N 1/08* (2006.01)

(52) U.S. Cl.
CPC ............. *H01Q 1/44* (2013.01); *A61N 1/0587* (2013.01); *H01Q 1/2225* (2013.01); *A61N 1/3624* (2013.01); *A61N 1/37229* (2013.01); *A61N 2001/086* (2013.01); *Y10T 29/49018* (2015.01)

(58) Field of Classification Search
USPC ...................................................... 607/5, 32
See application file for complete search history.

(56) References Cited

U.S. PATENT DOCUMENTS

| 7,899,555 B2 | 3/2011 | Morgan et al. |
| 2006/0009831 A1 | 1/2006 | Lau et al. |
| 2007/0055310 A1 | 3/2007 | Lau |
| 2009/0018599 A1* | 1/2009 | Hastings et al. ............ 607/32 |

FOREIGN PATENT DOCUMENTS

| EP | 1844812 B1 | 12/2009 |
| WO | 2005092431 A1 | 10/2005 |

* cited by examiner

*Primary Examiner* — Carl H Layno
*Assistant Examiner* — Jon Eric C Morales

(57) ABSTRACT

An intra-pericardial medical device is provided that comprises a lead body having a proximal portion, a distal end portion, and an intermediate portion extending between the proximal portion and the distal end portions. An intra-pericardial medical device further includes the control logic housed with the lead body and an energy source housed within the lead body. A stimulus conductor is included and extends along the lead body. An electrode is joined to the stimulus conduct near the distal end portion, where the electrode configured to deliver stimulus pulses. A telemetry conductor is provided within the lead and extends from the proximal portion and along the intermediate portion of the lead body. The telemetry conductor is wound into a series of coil groups to form inductive loops for at least one of receiving and transmitting radio frequency (RF) energy.

19 Claims, 12 Drawing Sheets

INTRA-PERICARDIAL MEDICAL DEVICE

BACKGROUND OF THE INVENTION

Embodiments of the present invention generally relate to implantable cardiac devices, and more particularly to intra-pericardial medical devices having a built-in telemetry system.

Implantable medical devices, for example, pacemakers, cardio-defibrillators, neurostimulators and the like, utilize leads to form the electrical connection between a device pulse generator and tissue or nerves that are to be stimulated. As is well known, the leads connecting such devices with the heart may be used for pacing or for sensing electrical signals produced by the heart, or for both pacing and sensing in which case a single lead serves as a bidirectional pulse transmission link between the device and the heart. The lead typically comprises a distal end portion for carrying a tip electrode and a ring electrode. The lead may also carry one or more cardioverting and/or defibrillation shocking electrodes.

Various lead types for different placement approaches have been developed, including endocardial and epicardial leads. For example, an endocardial type lead is one that is inserted into a vein and guided therethrough to a target location, for example, in one or both of the chambers of the right side of the heart or within one of the veins of the coronary sinus region of the heart for left side stimulation and/or sensing. The distal end portion of an endocardial lead may carry a helical, screw-in tip element, electrically active or inactive, and/or outwardly projecting tines or nubs and/or a sinuous shape for anchoring the lead.

There are factors, however, which warrant alternatives to a transvenous lead. These factors include coronary sinus and/or coronary venous obstructions. Furthermore, the location of the coronary veins effects the implant location of the electrode, which can make it difficult to place a left side lead in a specific preferred location and may lengthen or render unpredictable the amount of time needed to implant the lead. In addition, a portion of the patient population is unable to receive this type of lead due to vasculature anomalies. In such cases, epicardial or myocardial type leads may be used. Such leads are attached directly to the epicardium using sutures or other fixation mechanisms such as a helical screw-in electrode that engages the myocardium. Myocardial leads typically are used for temporary pacing or for permanent pacing following open-heart surgery.

Conventional approaches to the placement of epicardial leads usually involve thoracotomies or sternotomies. Such placement techniques have disadvantages.

To mitigate these disadvantages, minimally invasive lead placement techniques have been developed for placing a myocardial lead on the surface of the heart via a small, finger size opening in the chest. Such techniques may include the use of a fiber optics video camera of the type commonly used in other thoracic surgeries (for example, lung biopsies and other thoracic cavity and cardiac procedures) for visually imaging, and thereby aiding, the lead placement procedure. These minimally-invasive lead placement techniques allow for faster, safer and easier myocardial lead placements with significantly less morbidity, trauma and pain to the patient. Percutaneous access to the epicardial surface comprises an even less invasive technique, available not only to surgeons but to cardiologists as well.

Moreover, cardiac leads for conventional implantable medical devices experience at least some of the following limitations. Conventional cardiac leads afford limited access to only certain locations of the left atrium (LA) and left ventricle (LV) that are depend in part on vein location. Conventional cardiac leads are limited to pacing/sensing based timing for only certain combinations of electrodes due to the electrodes proximity to the RA, RV, LA and LV. Further, conventional cardiac leads create RF heating sources when in the presence of an MRI field if not corrected through added structure or circuits which increase size, complexity, cost and the like. Also, conventional cardiac leads, through their size and placement inside the myocardium, form conducting paths or loops that result from an antenna effect caused when the leads experience an RF field. Conventional cardiac leads, through their size and placement inside the myocardium, experience Eddy current flow that creates a risk of heating and cardiac stimulation. Further, conventional implantable medical device (IMD) systems may experience large forces and torques imposed thereon. These forces cause an undue risk of lead fracture near where the lead passes by the clavical bone. As the patient moves over time, the clavical bone wears on the lead and may fracture the lead.

There is a desire to move towards a satellite pacing system as a potential future trend for less mechanical lead issues and MRI safety. Satellite pacing systems are appealing, but thus far have faced various challenges in implementation, such as for dual chamber pacing or atrio-ventricular (AV) synchrony. For example, it has been proposed to provide a satellite pacing system having one or more slave pacing components located on or in the heart and a master pacemaker controller located where a conventional IMD is positioned. The slave pacing components include a sensing and pacing electrode(s) located at a desired position about the heart. The slave pacing components communicate with the master pacemaker controller. The master pacemaker controller represents a conventional pacemaker or implantable cardioverter-defibrillator (ICD). In this proposed satellite pacing system, conventional leads are not useable.

However, this master/slave configuration has experienced certain difficulties. As one example, the communications link to the slaves is difficult to maintain and use an undue amount of power to maintain.

There remains a need for an improved implantable medical device.

SUMMARY

In accordance with one embodiment an implantable medical system is provided that includes an intra-pericardial medical device (IPMD) located in the intra-pericardial SAC. The IPMD includes a telemetry system integrated therein. The IPMD affords one or more of the following: i) free access to locations of the right atrium (RA), left atrium (LA), right ventricle (RV), and left ventricle (LV); ii) pacing/sensing based timing of any desired combination of the RA, RV, LA and LV; iii) reduces RF heating sources to provide a system that is MRI safe; iv) removes conductors from inside the myocardium, thereby avoiding the formation of conducting paths/loops that would otherwise result from an antenna effect in RF fields; v) avoids Eddy current flow that would otherwise create a risk of heating and cardiac stimulation; vi) provides conductors with comparable wavelength are no longer existing so that antenna effect or eddy currents is eliminated; vii) avoids large force and torque thereon because of the small size; viii) provides an innovative telemetry antenna design allows good coupling between the antenna around the heart and an external antenna; ix) enables use of a rechargeable battery, and x) avoids lead fractures caused by rubbing against the clavical bone.

In accordance with an embodiment, an IPMD is provided that comprises control logic, an energy source and charge storage device. A lead body has a proximal portion, a distal end portion, and an intermediate portion extending between the proximal portion and the distal end portions. A stimulus conductor is included and extends along the lead body. A terminal joins to the stimulus conduct near the proximal portion of the lead body. The terminal is configured to be joined to the energy source and/or charge storage device for a stimulus pulse. An electrode is joined to the stimulus conduct near the distal end portion, where the electrode configured to deliver stimulus pulses. A telemetry conductor is provided within the lead and extends from the proximal portion and along the intermediate portion of the lead body. The telemetry conductor is wound into a series of coil groups to form inductive loops for at least one of receiving and transmitting radio frequency (RF) energy.

In accordance with an embodiment, the intermediate portion of the lead body extends along a longitudinal axis. The intermediate portion including a series of loop segments distributed along the longitudinal axis. The loop segments have opposed sides aligned in a common plane. The loop segments have a perimeter that is flared in a direction laterally with respect to the longitudinal axis of the lead body. Each of the loop segments includes at least one of the coil groups.

In accordance with an embodiment, the intermediate portion of the lead body includes a series of flared segments joined by linking regions. Each of the flared segments has a pair of opposed sides separated by a thickness of the flared segment. Each of the flared segments includes at least one of the coil groups. Optionally, the intermediate portion of the lead body may include a series of disc-shaped segments configured to lie in a common plane, where each of the disc-shaped segments includes one of the coil groups enclosed within an insulated shell.

In accordance with an embodiment, the telemetry conductor may be wound in a manner to receive and transmit RF energy that represents communications signals to and from an external programming device. Optionally, the telemetry conductor may be wound in a manner to receive RF energy that represents power to charge an implantable medical device joined to the proximal portion of the lead body.

Optionally, each of the coil groups may include a series of windings connected in series and distributed along the intermediate portion of the lead body. Optionally, each of the coil groups may include at least one winding of the telemetry conductor. Optionally, at least one of the coil groups may include multiple windings that are at least partially spatially overlapped with one another.

In accordance with an embodiment, the intermediate portion of the lead body extends along a longitudinal axis, and the coil groups are distributed along the intermediate portion and positioned to be centered upon the longitudinal axis.

In accordance with an embodiment, the distal end portion represents a precurved distal end portion that has a distal end and a proximal end. A flexible loop member is carried by the distal end portion and has a proximal segment attached to the proximal end of the distal end portion and a distal segment attached to the distal end of the distal end portion. The loop member may have a normally expanded state in which side portions of the loop member are spaced from the precurved distal end portion, and may be adapted to assume a contracted state in response to the precurved distal end portion assuming a straightened configuration. The electrode carried by the precurved distal end portion.

DETAILED DESCRIPTION

Embodiments of the present invention provide an intra-pericardial medical device (IPMD) having, among other things, a unique telemetry design that is integrated into a lead body with pacing/sensing leads. The IPMD may be stretched to desired locations, such as LA and LV or traditional RA and RV or other combinations of the four heart chambers (RA, LA, and RV and LV). A small pacemaker unit (e.g. nanopacer) may be located at an intermediate position (e.g. the center) along the lead body of the IPMD. The pacemaker unit may be positioned at an intermediate position with a telemetry antenna or, alternatively, at other locations such as at ends or a center point along the telemetry antenna and/or lead body.

Embodiments disclosed herein are directed to IPMDs that facilitate and enhance the accurate placement (and monitoring of such placement) of medical electrodes. Although embodiments may be used in a variety of medical procedures, they are suited for installation as a cardiac device into the pericardial space of the heart. This installation may be made, for example, via percutaneous subxiphoid procedures. By way of example only, U.S. Pat. No. 7,899,555 describes various ways in which the leads may be placed and then used. The complete and entire subject matter of U.S. Pat. No. 7,899,555 is expressly incorporated herein by reference in its entirety.

Figure 2:
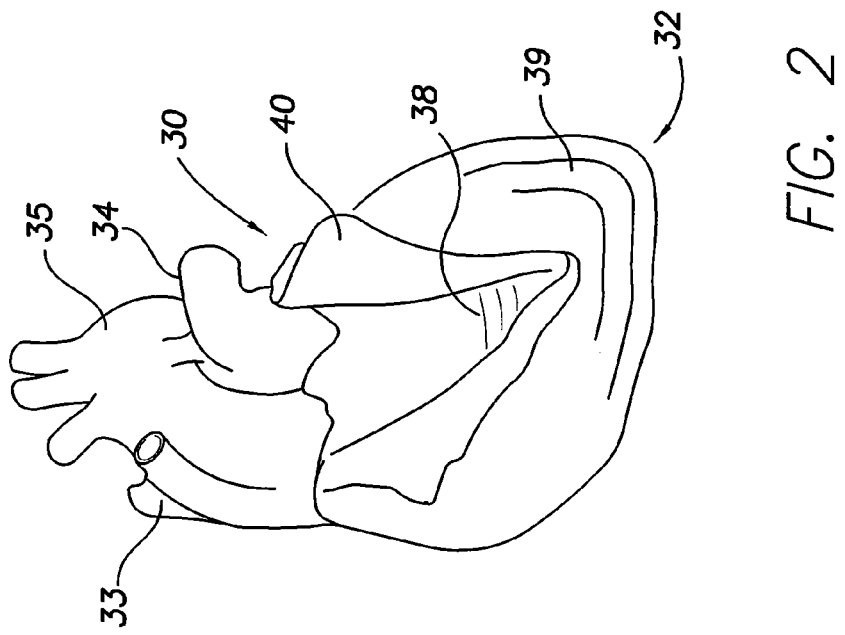
FIG. 2 is a perspective view of the heart of FIG. 1 with the pericardium partially opened to reveal the myocardium.
Figure 1:
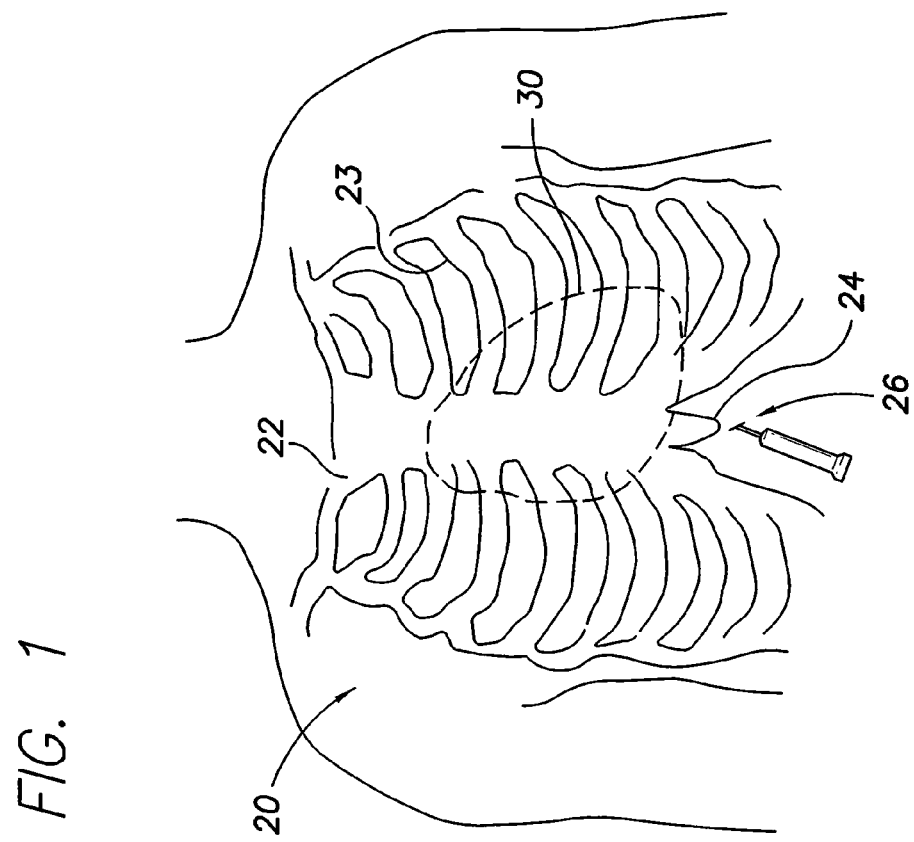
FIG. 1 is a front view of a human rib cage and the heart therein.

FIGS. 1 and 2, respectively, illustrate these structures and, in particular, the reference numeral 20 in FIG. 1 schematically illustrates the human chest and shows the sternum 22 and the ribs 23 which attach to the sternum. The ribs and the sternum form a "rib cage" which provides a protective covering around the heart, lungs and other vital organs. Positioned at the lower end of the sternum 22, is the xiphoid process or cartilage 24. The region 26 immediately below the xiphoid process is commonly referred to as the subxiphoid region. Finally, lying within the rib cage is the heart 30 (shown in broken lines).

A perspective view of the heart 30 is shown in FIG. 2. The body of the heart extends upward from an apex 32 to where it joins with various vein and artery structures that make up the heart's blood vessels. For example, the superior vena cava 33 is one of the major vessels which pass oxygen-depleted blood from the body into the right atrium of the heart. A pair of pulmonary arteries 34 (only one shown) route blood from the right ventricle to the lungs. After oxygen-rich blood is returned from the lungs to the left atrium, the left ventricle pumps it out to the body through the aortic arch 35.

Surrounding the body of the heart 30 is the pericardium 40 which is a double walled sac of fibrous tissue that surrounds the heart up to the roots of the heart's blood vessels. In FIG. 2, the pericardium 40 has been cut and folded back to reveal the myocardium 38 which is the muscular tissue that principally forms the walls of the heart. The myocardium 38 is again shown in FIG. 3 which is an enlarged section through the heart wall. A membrane known as the endocardium 39 forms an inner lining of the myocardium and, as shown, the pericardium 40 overlies the myocardium.

An outer portion of the pericardium is the fibrous pericardium which is formed of dense connective tissue to protect the heart and anchor it to chest structures (e.g., the diaphragm and the back of the sternum). The inner portion of the pericardium is the serous pericardium which has two layers. The outer layer is the parietal pericardium which lies next to the fibrous pericardium. The inner layer is the visceral pericardium which is typically called the epicardium.

The fibrous pericardium 41 and parietal pericardium are collectively referred to as the "pericardial sac." The parietal and visceral layers are spaced apart to form the pericardial space which is filled with serous fluid generally called the pericardial fluid. The pericardial fluid acts to reduce surface tension and facilitate free movement of the myocardium. The term epicardial is typically used to refer to the outside surface of the heart.

In accordance with at least certain embodiments, the cardiac lead may be configured for insertion along an insertion path through the pericardial sac and into the pericardial space to facilitate secure attachment to the epicardium. Examples of methods for placing an IPMD are described in the '555 patent.

Figure 3A:
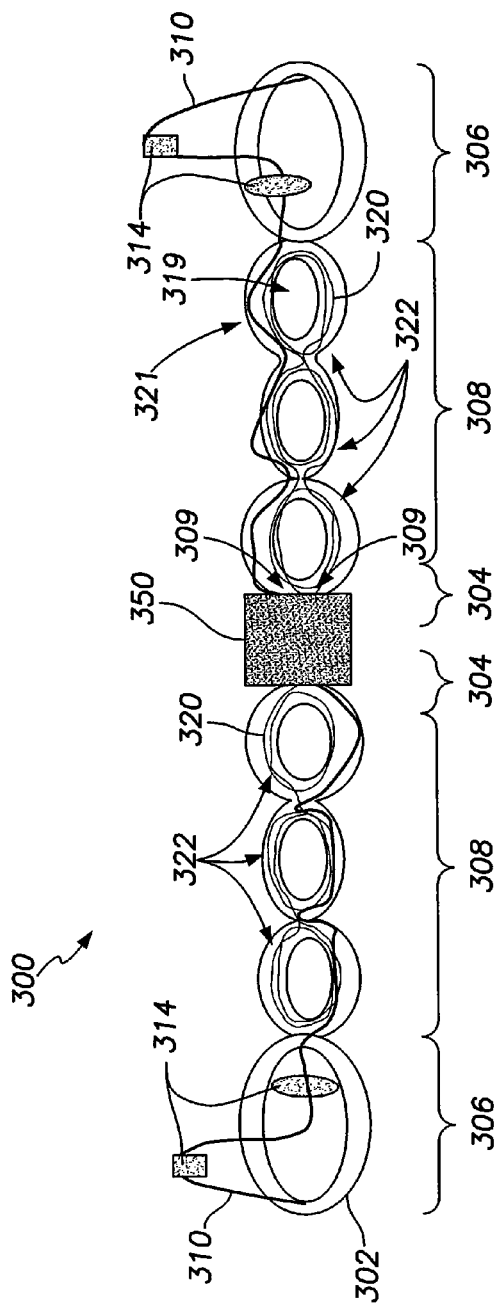
FIG. 3A illustrates an IPMD formed in accordance with an embodiment of the present invention.

FIG. 3A illustrates an IPMD device 300 formed in accordance with an embodiment of the present invention. The device 300 comprises a lead body 302 having a proximal portion 304, a distal end portion 306, and an intermediate portion 308 extending between the proximal portion 304 and the distal end portion 306. The lead body 302 includes a series of loop segments 321 that have openings 319 through center regions of each loop segment 321 (e.g., similar to a donut). The device 300 includes one or more sensing and/or stimulus conductors 310 extending along the lead body 302. The number of conductors 310 will depend on the number of unique electrodes provided. Optionally, the device 300 may include one or more screws or helix to secure the lead body 302 to the myocardium for fixation and as a pacing/sensing lead. The conductors 310, 320 may be bundled together and wound co-radially, but insulated from one another.

The conductors 310 may be used to deliver lower energy or high energy stimulus, such as pacing pulses, cardioverter pulse trains, defibrillation shocks and the like. The conductors 310 may also be used to sense electrical activity, such as physiologic and pathologic behavior and events. Each conductor 310 is electrically isolated from the other conductors 310 and from the telemetry conductor 320. Terminals 309 and 312 are joined to the stimulus and telemetry conductors 310 and 320, respectively, near the proximal portion 304 of the lead body 302. The terminal 309 is configured to be joined to an energy source, such as an IMD. The terminal 309 receives stimulus pulse(s) from the IMD. One or more electrodes 314, 315 are joined to the conduct 310. The electrode(s) 314, 315 may be the same or different size and may be located near the distal end portion 306 and/or at various positions along the intermediate portion 308. The electrodes 314, 315 are configured to deliver high or low energy stimulus pulses to the myocardium. The electrodes 314, 315 may be also used to sense electrical activity of the myocardium.

Figure 3B:
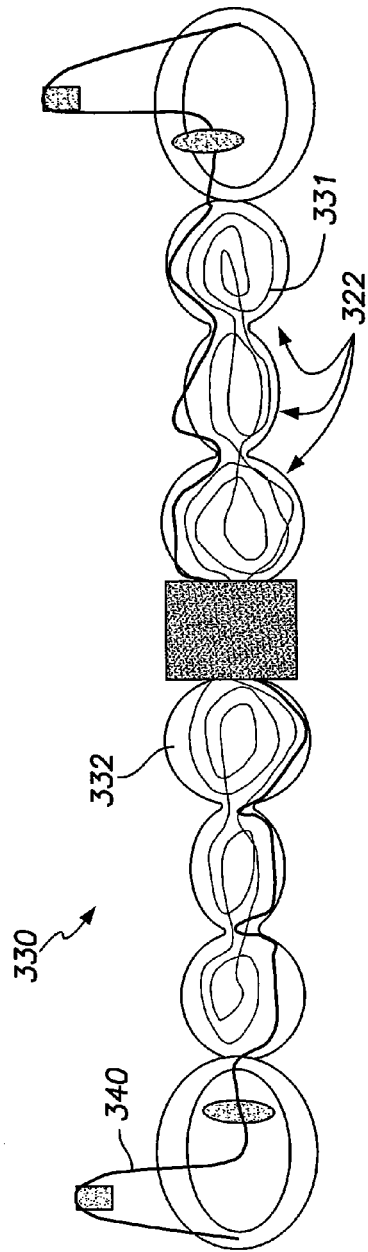
FIG. 3B illustrates an IPMD formed in accordance with an embodiment of the present invention.

A telemetry conductor 320 is provided within the lead body 302 and positioned to extend from the proximal portion 304 and along the intermediate portion 308 of the lead body 302. The telemetry conductor 320 includes winding that is wound into a series of coil groups 322 to form inductive loops. The coil groups 322 operate to receive and/or transmit radio frequency (RF) energy. The windings in the coil groups 322 may be formed in a variety of patterns from generally uniformly shaped circles, ovals and the like. However, the windings or inductive loops of the coil groups 322 are wound in a uniform shape and each coil group 322, that is connected in series, is wound in a common direction about a corresponding axis. For example, if one winding is wound in a clock-wise direction about an axis of the associated coil group, then all of the windings joined in series therewith should be wound in the same clock-wise direction about the same axis or associated axes of other coil groups. Alternatively, if one winding is wound in a counter-clock-wise direction about an axis of the associated coil group, then all of the windings joined in series therewith should be wound in the same counter-clock-wise direction about the same axis or associated axes of other coil groups. In the examples of FIGS. 3A and 3B, the telemetry conductor 320 is not shown in any specific winding pattern. But it is understood, that the telemetry conductor 320 may be wound in any desired manner to receive and transmit RF energy that represents communications signals to and from an external programming device. Alternatively, or in addition, the telemetry conductor 320 may also be wound in a manner to receive RF energy that represents power which is then used to charge an implantable medical device joined to the proximal portion 304 of the lead body 302. The terminal 312 receives signals (e.g., power or data) induced into the telemetry conductor 320 by RF energy passing about the coil groups 322. The coil groups 322 include at least one partial winding of the telemetry conductor 320. Optionally, at least one of the coil groups 322 may includes multiple windings that are at least partially spatially overlapped with one another. The coil groups 322 are distributed along the intermediate portion 308 and positioned to be centered along a longitudinal axis. The conductor 320 is surrounded by a thin film insulation (e.g., Silicone, OPTIM, polyurethane) to electrically separate adjacent windings such that the inductive loops of each coil group 322 are insulated from one another (e.g., ETFE).

FIG. 3B illustrates an IPMD 300 formed in accordance with an embodiment of the present invention. The lead 330 comprises a lead body 332 having a proximal portion, a distal end portion, and an intermediate portion extending between the proximal portion and the distal end portion. The lead 330 includes one or more sensing and/or stimulus conductor 340 extending along the lead body 332. A telemetry conductor 331 is provided within the lead body 332 and positioned to extend from the proximal portion and along the intermediate portion of the lead body 332. The telemetry conductor 331 is wound into a series of coil groups 333 to form inductive loops. The number of loop segments 321 and windings per loop segment 321 may vary based on the desired amount of inductance. When more than one intermediate segment 308 is used, then the coil groups 322 are connected in series such that the total inductance is the sum of the individual inductance of each coil group 322. The coil groups 322 operate to receive and/or transmit radio frequency (RF) energy. The lead body 332 is formed as a solid body without opening there through similar to the opening 319 in the loop segments 321 in the embodiment of FIG. 3A.

Returning to FIG. 3A, an intra-pericardial lead control block 350 is provided within the lead body 302. The components within the control block 350 and related functions may vary dependent upon the implementation. By way of example, the control block 350 may include all of the control logic needed to implement an implantable medical device, such as but not limited to an implantable pacemaker, cardioverter, defibrillator, neurostimulator and the like. The control block 350 includes one or more energy sources such as a battery, a rechargeable battery and the like. The control block 350 may also include a charge storage device depending upon the functionality to be performed. For example, if the IPMD 300 delivery stimulus pulses, the charge storage device may include one or more capacitors that are sufficient in capacity to deliver the desired stimulus. Alternatively, the control block 350 may have a more limited subset of components configured to implement only a portion of the functionality available in an implantable medical device.

Figure 3C:
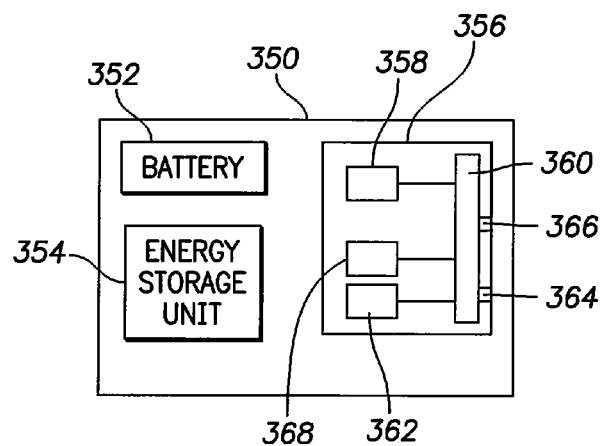
FIG. 3C illustrate a block diagram of a control block that may be included within the cardiac leads formed in accordance with embodiments of the present invention.

FIG. 3C illustrates a block diagram of a control block 350 that may be included within the leads described herein. In the example of FIG. 3C, the control block is implemented to include all of the functionality of an IMD. The control block 350 includes a battery 352, an energy storage unit 354 such as capacitors. The energy storage unit 354 will vary depending upon the functionality desired to be supplied by the control block 350. For example, when the control block 350 affords all of the functionality of a defibrillator, the storage 354 will represent high voltage capacitors capable of storing large amounts of energy needed to deliver defibrillation shocks.

Control logic is provided on an integrated circuit (IC) 356 is housed in the control block 350. The control logic includes various electronic components based on the desired functionality of the control block 350. By way of example, the control logic on the IC 356 includes a processor 358, a switching bridge 360, and analog-to-digital (A/D) converters 362. The switch bridge 360 includes multiple inputs 364 and 366 that are configured to be coupled to the terminals 312 and 309 (FIG. 3A) on the telemetry and stimulus conductors 320 and 310, respectively. Optionally, the stimulus and telemetry conductors 320 and 310 may be directly connected to the inputs 364 and 366 of the switch bridge 360. Optionally, more inputs 364, 366 may be used based on the number of electrodes and telemetry coils.

The IC 356 may also include a transceiver 368 that is configured to receive signals that are detected by the telemetry conductor 320, as well as transmit signals to the telemetry conductor 320 that are then wirelessly transmitted as RF energy. For example, the telemetry conductor 320 may receive, in the RF energy, data signals such as commands, parameters, thresholds and the like. As one optional exemplary implementation for incoming data, the transceiver 368 may detect analog data signals sensed by the coil groups 322, convert the analog data signals into digital data packets and convey the data packets to the processor 358. As one optional exemplary implementation for outgoing data, the transceiver 368 receive data packets from the processor 358, convert the data packets to analog data signals and transmit the analog data signals over the coil groups 322. Optionally, for outgoing data transmissions, the transceiver 368 may packetize data segments in accordance with a predetermined wireless transmission protocol, such as by dividing an outgoing data stream into segments, and packetize each data segment with header and footer information. Similarly, incoming data transmissions may be formatted in accordance with a predetermined transmissions protocol. The transceiver 368 may temporally buffer incoming data transmissions, parse the stored inbound data stream for header and/or footer information, and extract the data content from the inbound data stream. The transceiver 368 may then convey data content to the processor 358 with or without reformatting and/or repackaging the data content.

Optionally, the battery 352 may be rechargeable and the telemetry conductor 320 may receive, in the RF energy, a power signal that is used to recharge the battery 352. Optionally, the telemetry conductor 320 may receive power in the RF signal that is routed directly to the energy storage unit 354 to directly charge capacitors before the capacitors deliver a low or high energy stimulus (e.g., pace or defibrillation.)

By way of example only, the control block 350 may represent a "nano" pacemaker that may be packaged in a very compact and small manner having a form factor substantially similar to the form factor of the lead body 302. For example, the battery 352, energy storage unit 354 and IC 356 may be packaged into a long tubular housing or a short, flat round disk within a metal case. The housing of the control block 350 may have a cross-section that is no larger than the cross-section of the lead body 302. Alternatively, the housing of the control block 350 may have a disc shape when viewed from the top down and have a small thickness or height, where the disc shape and the thickness/height are substantially the same as the disc shape and thickness of the lead body (e.g. as discussed in connection with FIGS. 4A and 4B).

In the example of FIG. 3A, the control block 350 is shown to be located at an intermediate position between opposed segments of the device 300, with a pair of intermediate portions 308 extending from opposite ends of the control block 350. Alternatively, the control block 350 may be located at any point along the length of the device 300, as well as at either end thereof. For example, the control block 350 may be positioned immediately adjacent to an electrode 314, with all of the coil groups 322 extending from the opposite side thereof.

The control block 350 may be configured to support one pair of electrodes 314 or multiple pairs of electrodes. In the event that a single control block 350 is configured to support multiple pairs of electrodes, the corresponding additional number of electrodes 314 would be distributed in desired positions along the device 300. In addition, a corresponding additional number of inputs 364, 366 would be provided at the switching bridge 360.

Optionally, the control block 350 may be configured to operate independently and entirely within the intra-pericardial region. The control block 350 may be configured to afford dual chamber pacing and/or dual chamber sensing.

When the device 300 is located deeper, nearer the heart wall, as compared with subcutaneous implants, the signals transmitted to/from the coil groups 322 may be weaker.

Optionally, more or fewer coil windings may be included within each coil group 322 depending upon whether the lead is intended to be implanted shallow or deeper. Embodiments described herein utilize waved multi-loop coil groups 322. Each coil group 322 represents an inductor. By joining the coil groups 322 in electrically in series, a series of inductors are formed to achieve coupling and signal linkage through telemetry with desired implanted or external components.

By way of example, the insulated wires of the conductors 310 and 320 are made of biocompatible metals (DFT or Copper etc). The coating of the wires can be ETFE and the wires may be embedded inside Silicone or another material. The device 300 is very flexible inside the pericardial SAC. The dimension of the lead (number of turns, size etc) may be varied based on the criteria of telemetry, clinical and mechanical requirements.

Figure 3D:
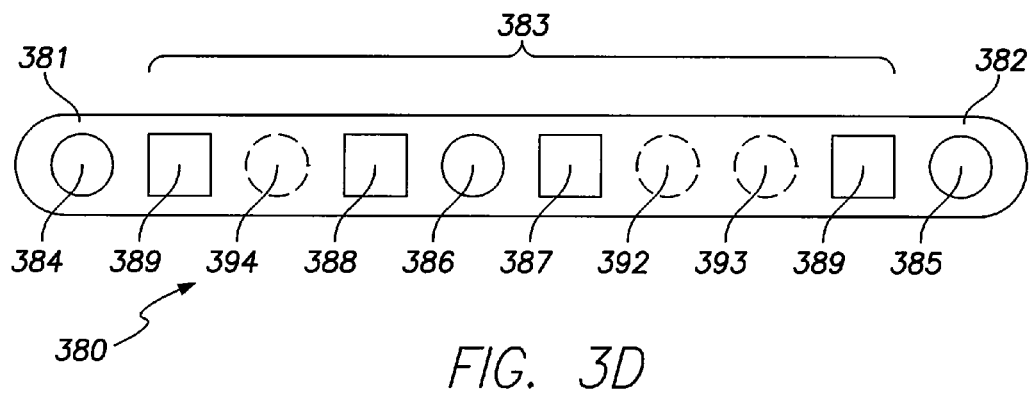
FIG. 3D illustrates an IPMD formed in accordance with an embodiment of the present invention.

FIG. 3D illustrates a lead 380 formed in accordance with an alternatively embodiment. The lead 380 includes distal end portions 381 and 382 separated by an intermediate portion 383. The distal end portions 381 and 382 have electrodes 384 and 385, respectively, to provide at least one of sensing and pacing at opposite ends of the lead 380. Optionally, the intermediate portion 383 may also include one or more electrodes 386. The electronic components of an implantable medical device are separated and distributed along the length of the lead 380. For example, a battery 387 may be located at one position along the lead 380, while a control block 388 is located at another position along the lead 380. One or more energy storage units 389 may be located at another position along the length 380. The battery 387, control block 388 and energy storage units 389 are separated from one another and housed within separate segments of the body of the lead 380.

The lead 380 also includes one or more coil groups 392-394 formed from a telemetry conductor wound into coil windings as discussed throughout. The coil groups 392-394 may be connected in series to form a series of inductors. Alternatively, the coil groups 392-394 each may be formed with electrically separate conductors such that each coil group 392-394 delivers a separate RF signal to the control block 388. Optionally, the coil groups 392 and 393 may be joined in series, while coil group 394 is maintained electrically separate. The electrodes 386 and coil groups 392-394 may be located between the battery 387, control block 388 and energy storage units 389.

In accordance with at least one embodiment, the loop segments 404 of the lead body can be formed to be squeezable or compressible into a catheter. A guiding wire can be attached to the lead during the implant. After the lead is in place, the catheter is extruded to the last loop with a guiding wire holding it. Pacing/sensing tests can be done before the system is completely released. If another attempt of location is needed, the guiding wire would be able to retract the system.

Figure 3E:
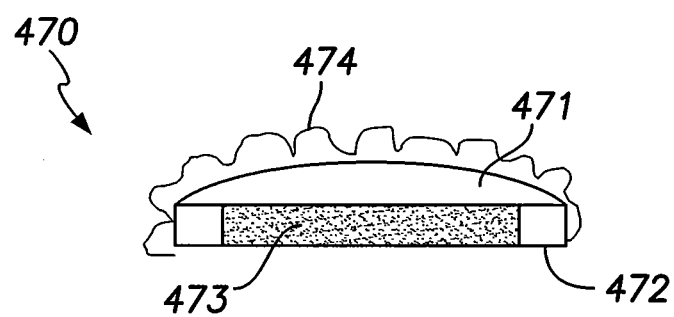
FIGS. 3E and 3F illustrate alternative embodiments for IPMD housings in accordance with various embodiments.

FIG. 3E illustrates an alternative embodiment for a housing 470 for a control block. The housing 470 is disc shaped with a flat top 471 and a bottom 472. The control logic, battery and energy storage unit are held with the interior cavity 473. A securing element 474 is provided about at least a portion of the exterior surface of the housing 470 of the control block. The securing element includes bumps or another form of rough surface formed of a biocompatible, flexible material. The securing member 474 is contoured to facilitate securing and stabilizing the housing 470 at one location against the heart surface within the pericardial sac.

Figure 3F:
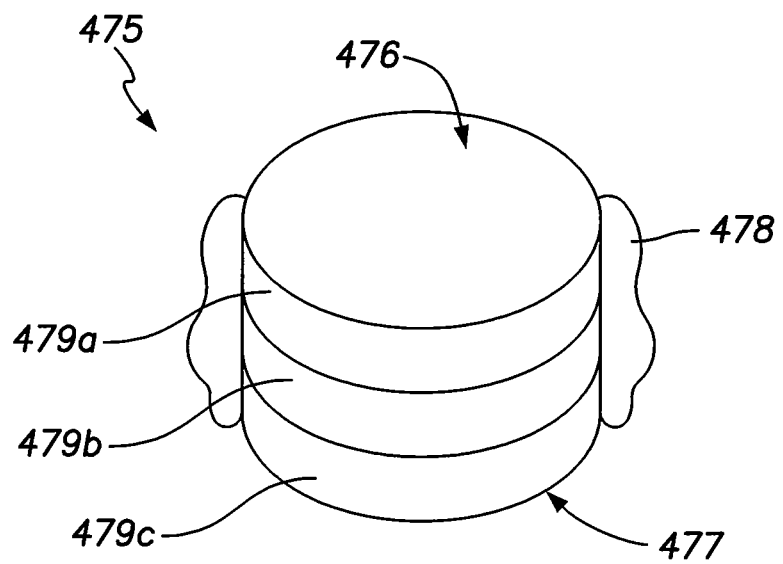

FIG. 3F illustrates an alternative embodiment for a housing 475 for a control block. The housing 475 is tubular shaped with a flat top 476 and a bottom 477. The control logic, battery and energy storage unit are held with an interior cavity in the housing 475. A securing element 478 is provided about at least a portion of the exterior surface of the housing 475 of the control block. The housing 475 includes a series of tube-sections 479A-479C stacked on one another. One of the tube-sections 479A-479C may include the control logic, while two or more other tube-sections 479B and 479C include energy storage units and/or batteries. The number of tube-sections 479B and 479C may vary depending upon the energy demands of the IPMD and upon the life time over which the IPMD is intended to operation. For example, an IPMD that is only intended to last 2 years may include tube-section 479B with one battery, while an IPMD that is only intended to last 10 years may include several tube-sections 479B each with a separate battery. As another example, an IPMD that is only intended to deliver low energy may include one tube-section 479C with one set of small capacitors, while an IPMD that is only intended to delivery high energy may include several tube-sections 479C that collectively include multiple capacitors connected in a manner to deliver a large effective capacitance and thus store and deliver high energy shocks.

Figure 4A:
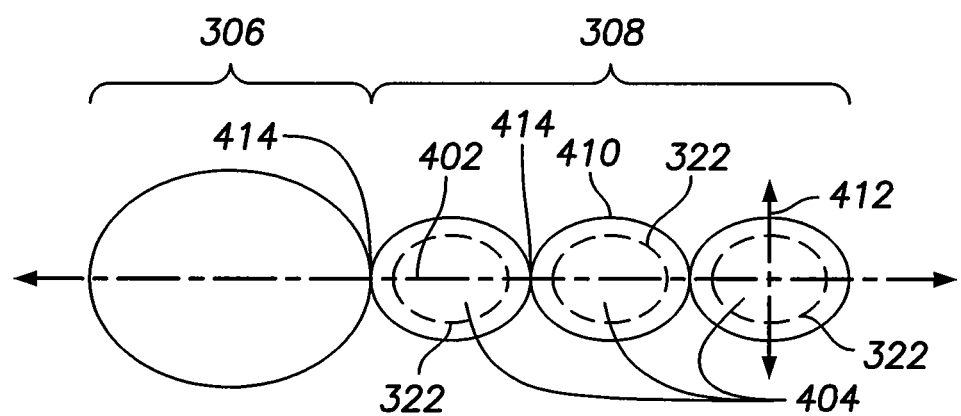
FIG. 4A illustrates a top plan view of a portion of a lead body formed in accordance with an embodiment.
Figure 4B:
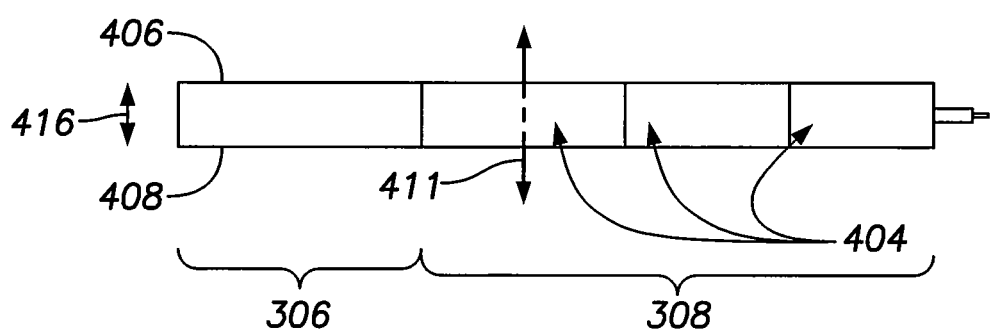
FIG. 4B illustrate a side view of a portion of a lead body formed in accordance with an embodiment.

FIGS. 4A and 4B illustrate an enlarged top plan view and a side view, respectively, of a portion of the lead body 302 formed in accordance with an embodiment. As shown in FIG. 4A, the distal end portion 306 and the intermediate portion 308 of the lead body 302 extend along a longitudinal axis 402. A lateral axis 412 extends orthogonal to the longitudinal axis 402 in a direction of a width of the lead body 302. In FIG. 4B, a transverse axis 411 is illustrated in a vertical or height direction. The longitudinal, lateral and transverse axes 402, 412 and 411 are orthogonal to one another and will be used throughout to describe general placement and orientation of the telemetry conductor 320. It is recognized that, while FIG. 4A illustrates the longitudinal axis 402 aligned in a straight manner, this is for illustration purposes only. When implanted, the lead body 302 and thus the longitudinal axis 402 will curve and wrap to follow the epicardium and/or to conform to a contour of an exterior of the heart or other tissue in a manner determined by the implanting physician. The intermediate portion 308 includes a series of loop segments 404 that are distributed along the longitudinal axis 402 and located adjacent to one another.

In the illustration of FIG. 4A, the loop segments 404 are located immediately adjacent one another and are formed integral with one another. The loop segments 404 may be joined with one another by linking regions 414. The intermediate portion 308 is also joined to the distal end portion 306 through a linking region 414. The loop segments 404, linking regions 414 and distal end portion 306 are formed integral with one another from a biocompatible electrically insulating material, such as silicon, polyurethane, or other materials such as copolymers (e.g., the Optim® insulation offered by St. Jude Medical).

The loop segments 404 have a perimeter 410 that is flared (e.g., diverges and then re-merges) in a direction generally toward and away from the lateral axis 412 with respect to the longitudinal axis 402 of the lead body 302. The loop segments 404 may have different contour shapes. By way of example, the loop segments 404 may have a perimeter, when viewed from the top down, that is disc-shaped, oval, circular, tubular, rectangular, triangular, and the like.

As shown in the side view of FIG. 4B, the loop segments 404 have opposed top and bottom sides 406 and 408 that are aligned generally in parallel planes that extend in a generally common direction as the longitudinal axis 402. The loop segments 404 are aligned along a common path. The pair of opposed top and bottom sides 406 and 408 are separated by a thickness 416 of the flared loop segments 404. The lead body 302 is formed of a flexible insulation. Therefore, it is recognized that, while FIG. 4B illustrates the loop segments 404 aligned in a straight manner, this is for illustration purposes. When implanted, the loop segments 404 will curve and wrap to follow the epicardium and/or to conform to a contour of an exterior of the heart in a manner determined by the implanting physician.

Each of the loop segments 404 include at least one of the coil groups 322 (denoted in dashed lines). The coil groups 322 are surrounded by a biocompatible electrically insulated material forming a shell. The shell hermetically encloses the sensing/stimulus conductor 310 and the telemetry conductor 320.

Figure 5A:
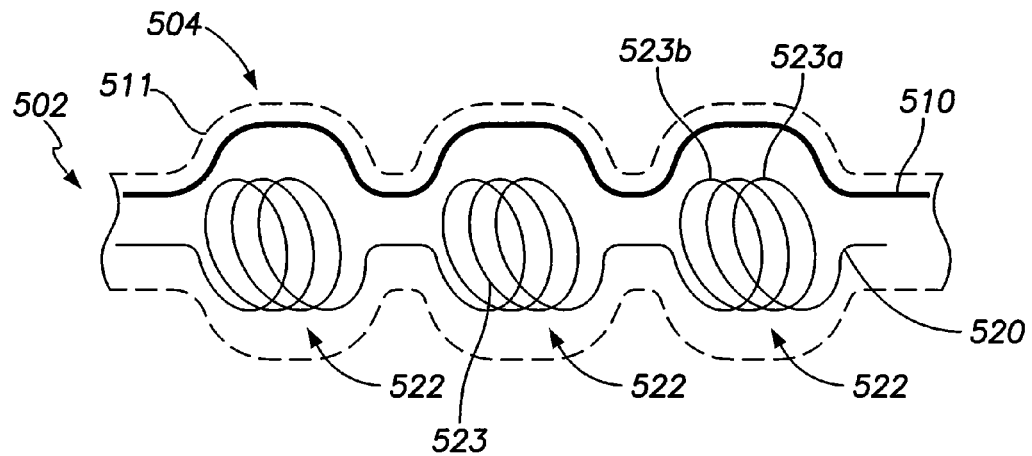
FIGS. 5A-5C illustrates examples of conductor layouts that may be implemented for the stimulus and telemetry conductors within a portion of a lead body in accordance with an embodiment.
Figure 5B:
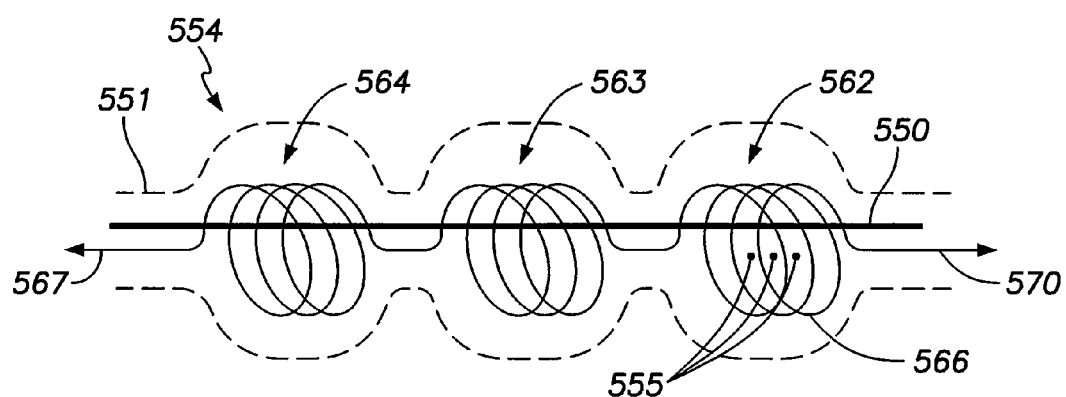
Figure 5C:
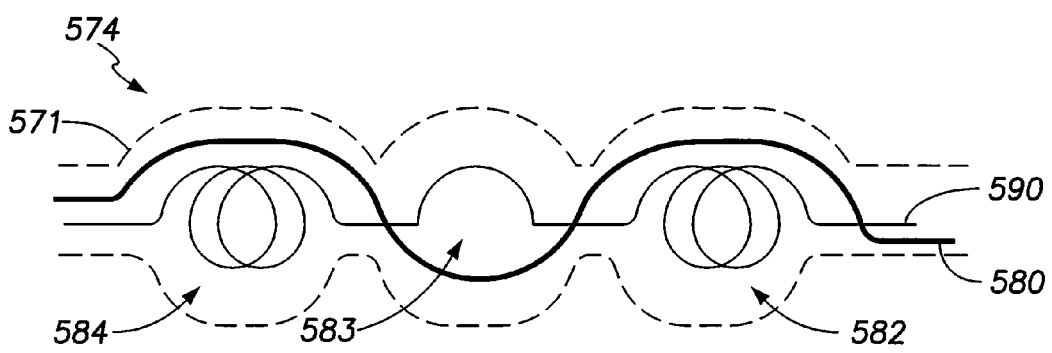

FIGS. 5A-5C illustrates examples of conductor layouts that may be implemented for the stimulus and telemetry conductors within a portion of a lead body 502. In FIG. 5A, a stimulus conductor 510 and telemetry conductor 520 are illustrated in connection with three body segments. The perimeter 511 of the body segments 504 is denoted in dashed lines. The telemetry conductor 520 includes a series of coil groups 522 within the body segments 504. The coil groups 522 include a series of coil windings 523 that are connected in series and distributed along the intermediate portion of the lead body 502. In the example of FIG. 5A, each coil group 522 includes an equal number of coil windings 523, namely three coil windings. Optionally, any number of coil windings 523 may be provided within each body segment 504 (e.g. 5, 10, 25, etc.). Optionally, a different number of coil windings 523 may be provided in each body segment 504 (e.g., 10 windings in the first body segment, 5 windings in the second body segment, and the like).

The coil windings 523 within each coil group 522 may be formed coaxially, namely having a common center point and a common radius. The coil windings 523, within a single coil group 522, may be stacked in the direction of the transverse axis extending out of the page in FIGS. 5A to 5C (411 in FIG. 4B). In this example, the coil windings 523 would be stacked such that the coil windings are aligned in parallel planes that are also generally aligned with the top and bottom sides 406 and 408 (FIG. 4B). Each of the coil groups 522 would include an upper outer winding 523A and a lower outer winding 523B located adjacent to the top and bottom sides 406 and 408 of the body segment 504.

Optionally, the coil windings 523 within a single body segment 504 may have different radius but be positioned about a common center point such that the coil windings are arranged concentric with one another.

The stimulus conductor 510 may be arranged to follow the perimeter 511 of the body segments 504 thereby forming a series of half waves. Optionally, a separate stimulus conductor (not shown) may be aligned to follow the opposite side of the perimeter in a mirrored image of the stimulus conductor 510.

FIG. 5B illustrates a conductor pattern having a stimulus conductor 550 and telemetry conductor 570 within body segments 554. The perimeter 551 of the body segments 554 is denoted in dashed lines. The telemetry conductor 570 includes a series of coil groups 562-564, each of which has a different number of coil windings 566. For example, the first coil group 562 may include 10 coil windings, while the second and third coil groups 563 and 564 include one and 20 coil windings, respectively. Within one or more of the coil groups 562-564, the coil windings 566 may be offset with respect to one another along a longitudinal axis 567 of the lead body. For example, within the coil group 562, each coil winding 523 may have a different center point 555 staggered along the longitudinal axis 567. In the example of FIG. 5B, the coil windings 566 may be wound in a common direction for all of the coil groups 562-564. Optionally, the coil windings 566 of coil group 562 and 563 may be wound in one direction (e.g., clockwise as viewed through the top side), while the coil windings 566 of coil group 564 are wound in an opposite direction (e.g., counter-clockwise as viewed through the top side). The stimulus conductor 550 is positioned to extend along the longitudinal axis 567 through the lead body. Optionally, the stimulus conductor 550 may extend generally through a central area of the lead body. The stimulus conductor 550 may be positioned adjacent the top or bottom side (e.g., 406 or 408 FIG. 4B) of the lead body. Optionally, the stimulus conductor 550 may be positioned at an intermediate height between the top and bottom sides 406 and 408 and extend between intermediate coil windings 566.

FIG. 5C illustrates a conductor pattern having a stimulus conductor 580 and telemetry conductor 590 within body segments 574 of a lead body. The perimeter 571 of the body segments 574 is denoted in dashed lines. The telemetry conductor 590 includes a series of coil groups 582-584. As one example, the coil group 583 may include half of one coil winding, while the coil groups 582 and 584 include a single complete winding or multiple coil windings. The stimulus conductor 580 is positioned to wrap in a sinusoidal manner about the coil groups 582-584 as the stimulus conductor 580 extends through the lead body.

Figure 6A:
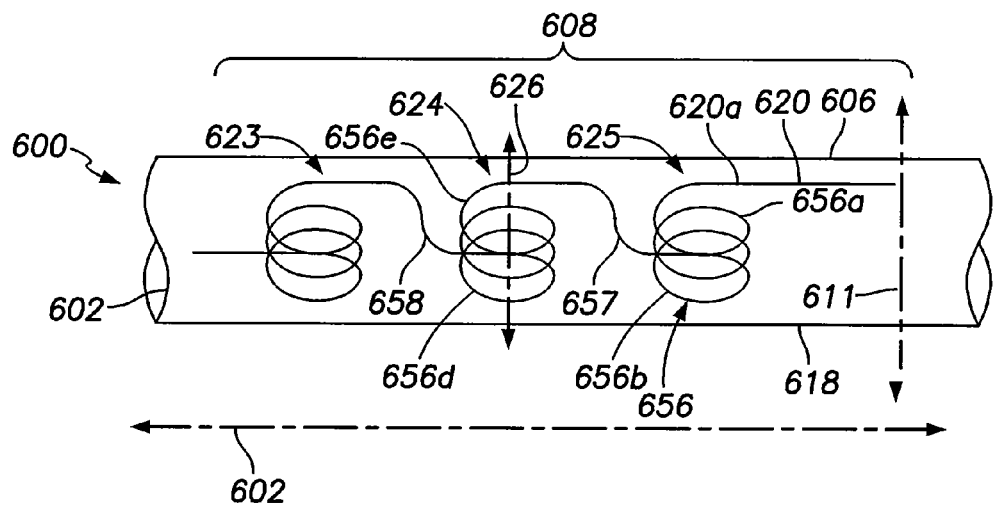
FIG. 6A illustrates a winding pattern for a telemetry conductor formed in accordance with an embodiment.

FIG. 6A illustrates a winding pattern 600 for a telemetry conductor 620 formed in accordance with an embodiment. The winding pattern 600 includes coil groups 623-625 held within an intermediate portion 608 of a lead body 602. FIG. 6A illustrates top and bottom sides 606 and 618 of the intermediate portion 608 of the lead body 602. The coil groups 623-625 are distributed along a longitudinal axis 602 and the coil windings 656 are stacked co-axially and vertically above one another. The coil windings 656 in coil group 625 are arranged co-axially along a common vertical axis 626 (e.g., along the direction of the transverse axis 611) such that an upper coil winding 656A is adjacent the top side 606 and a lower coil winding 656B is adjacent the bottom side 618.

FIG. 6A illustrates an example of how the winding pattern 600 may be laid out in the vertical or transverse direction across the thickness of the lead body. In particular, the telemetry conductor 620 has a proximal portion 620A that is located proximate the top side 606. The proximal portion 620A joins the upper coil winding 656A. The telemetry conductor 620 then spirals downward, from one coil winding to the next, toward the bottom side 618. The telemetry conductor 620 including an inter-group linking segment 657 that extends from the lower coil winding 656B of the first coil group 625 to an upper coil winding 656E of the second coil group 624. The telemetry conductor 620 spirals downward from the upper coil winding 656E through intermediate coil windings to a lower coil winding 656D in the second coil group 624. An inter-group linking segment 658 joins the coil windings 656 of the second and third coil groups 624 and 623 in a similar manner. The inter-group linking segments 657 and 658 span from an area adjacent to the bottom side 618 up to an area adjacent the top side 606. This pattern may be repeated for any desired number of coil groups.

Optionally, the winding pattern 600 may be modified such that the coil windings 656 in each coil group 623-625 spiral upward. For example, the inter-group linking segment 657 may extend from the upper coil winding 656A downward to join the lower coil winding 656D in the second coil group 624. The telemetry conductor 620 would then spiral upward in the second coil group 624 from the bottom side 618. In this example, the inter-group linking segment 658 would then extend from the upper coil winding 656E downward to join the lower coil winding in the third coil group 623. The telemetry conductor 620 would then spiral upward in the third coil group 623 toward the upper side 606.

Figure 6B:
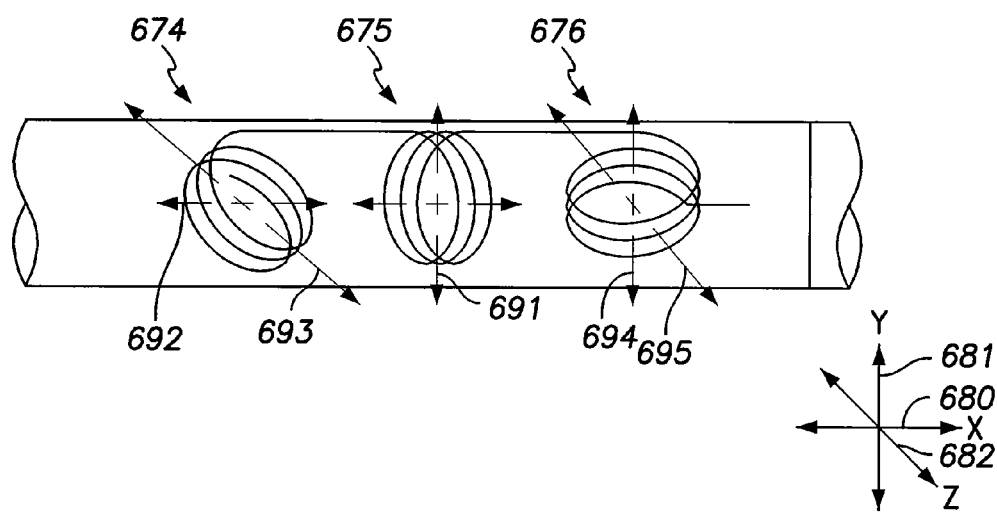
FIG. 6B illustrates a winding pattern for a telemetry conductor formed in accordance with an embodiment.

FIG. 6B illustrates an alternatively example of a winding pattern 670 formed in accordance with an embodiment. FIG. 6B illustrates a portion of a lead body 672 with coil groups 674-676. The lead body 672 extends along a longitudinal axis 680 (X-axis), has a height extending in the direction of a transverse axis 681 (Y-axis) and has a width extending in the direction of a lateral axis 682 (Z-axis). The coil group 675 is wound about an axis 690 that extends parallel to the longitudinal axis 680 of the lead body 672. The windings in the coil group 675 are aligned parallel to an X-Y plane defined by axes 690-691 which extend parallel to the longitudinal and transverse axes 680 and 681. The coil group 674 is wound about an axis 693 that extends parallel to the lateral axis 682 of the lead body 672. The windings in the coil group 674 are aligned parallel to an X-Z plane defined by axes 692-693 which extend parallel to the longitudinal and lateral axes 680 and 682. The coil group 676 is wound about an axis 694 that extends parallel to the transverse axis 681 of the lead body 672. The windings in the coil group 676 are aligned parallel to a Y-Z plane defined by axes 694-695 which extend parallel to the transverse and lateral axes 681 and 682. The coil groups 674-676 may be wound, in a common winding direction, but about different axes such that windings of each coil group 674-676 are aligned parallel to different planes (e.g., one or more groups parallel to the longitudinal axis, one or more groups parallel to the transverse axis, one or more groups parallel to the lateral axis) in order to eliminate or reduce the effects of motion inside heart upon reception/transmission of RF signals. The orienting the coil groups 674-676 about different axes may increase (e.g. even maximize) the ability of the telemetry conductor within the lead to couple well with another internal or external RF source.

Optionally, a first loop may be aligned in an X-Y plane, while a second loop is aligned at a non-orthogonal angle thereto, such as at a 45 degree angle to the X-Z plane or the Z-Y plane. Optionally, a different number of loops may be aligned at a 90 degree angle with respect to the X-Y plane, and the like.

Figure 7A:
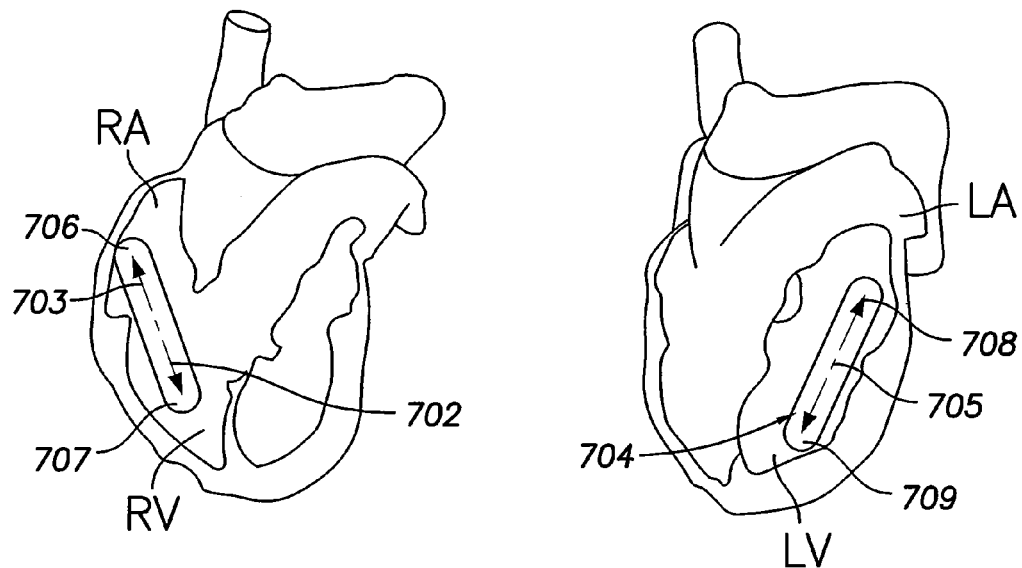
FIGS. 7A and 7B illustrate exemplary locations at which intra-pericardial leads may be inserted into the intra-pericardial sac in accordance with embodiments of the present invention.
Figure 7B:
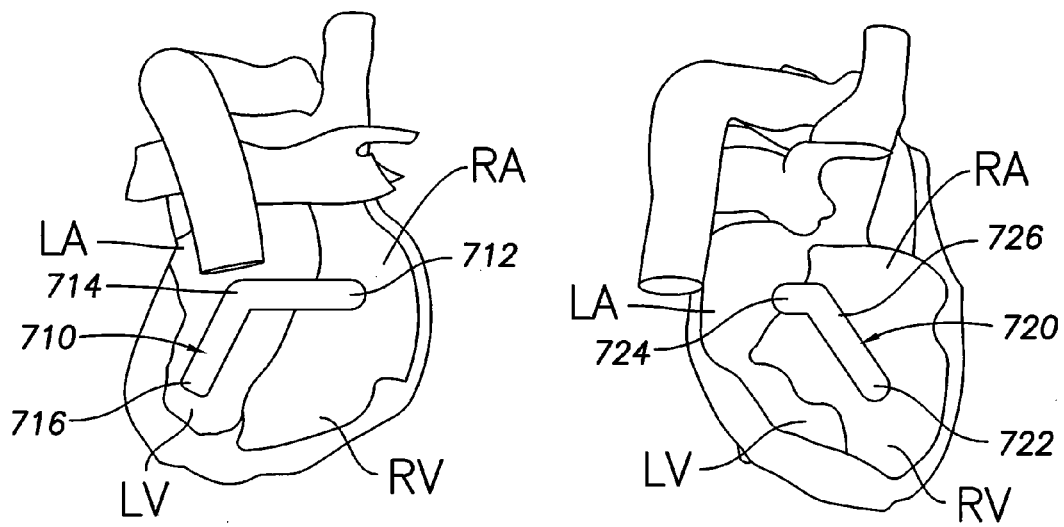

FIGS. 7A and 7B illustrate exemplary locations at which a lead, formed in accordance with embodiments herein, may be inserted into the intra-pericardial sac. In FIG. 7A, anterior and lateral views of the heart are illustrated. A lead 702 is located to extend between the RA and the RV, and a lead 704 positioned to extend between the LA and the LV. The lead 702 includes opposed ends 706 and 707 located proximate the RA and RV, respectively. The lead 704 includes opposed ends 708 and 709 located proximate to the LA and LV, respectively. The leads 702 and 704 are illustrated to be linear and to extend along longitudinal axes 703 and 705, respectively. Optionally, the leads 702 and 704 may have various shapes, such as being curved to wrap around desired regions of the heart. The ends 706-709 each include one or more electrodes for sensing and/or delivering pacing stimulus to afford dual chamber pacing and sensing.

In the dual chamber pacing/sensing configuration, pacing and sensing between the LA to LV afford a desired hemodynamic performance and desired timing algorithms. For example, timing the latest LA activation as measured directly from the LA affords a desirable measure or landmark when determining when and whether to pace the LV.

In example of FIG. 7B, posterior views are illustrated of the heart. In example of FIG. 7B, electrodes may be positioned to afford tri-chamber pacing and sensing including the RA, LA and LV. In example of FIG. 7B, an electrode 710 is positioned to extend from the RA at a distal end 712 to the LA at an intermediate point 714. The electrode 710 includes an opposed distal end 716 located near the LV. A second electrode 720 has a distal end 722 located near the RV, a distal end 724 located near the LA and an intermediate portion 726 extending proximate the RA. The leads 710 and 720 are shaped in a wide V-shape, but may be arranged in other shapes to cover desired regions of the heart.

Locating the device 300 within the intra-pericardial sac affords the capability to access a large variety of different heart regions. As shown in FIGS. 7A and 7B, the leads 702, 704, 710 and 720 are formed as flexible strips and extend across desired combinations of heart regions. For example, the leads may wrap over the RV and LV and extend to either the RA or LA to afford biventricular pacing in accordance with various configurations, such as atrial pace/sense: RA; biventricular: RV and LV, or atrial pace/sense: LA and biventricular pace: the RV and LV.

Optionally, a combination of leads may be utilized that afford four chamber pacing and sensing. For example, leads may wrap over all four chambers of the heart such that four chamber pacing and sensing is feasible. In addition to basic pacemaker functionality, the system is provided in accordance with various embodiments described herein allow for alternative algorithms for atrial fibrillation and atrial tachycardia detection and termination, as well as improved algorithms for ventricular tachycardia and ventricular fibrillation detection and termination.

In accordance with various embodiments described herein, the lead will experience low variations in bipolar sensing. Variation in bipolar sensing is reduced by aligning bipolar electrodes in different planes. The sensed signals are sensitive to a propagation direction as measured relative to a bipolar orientation. Then the lead is implemented without a separate "master" implantable device, it may be desirable for the lead, when inserted into the intra-pericardial sac, to perform bipolar sensing. To overcome high variability in bipolar sensing, the lead may utilize bipolar electrodes that are arranged in different planes.

Figure 8A:
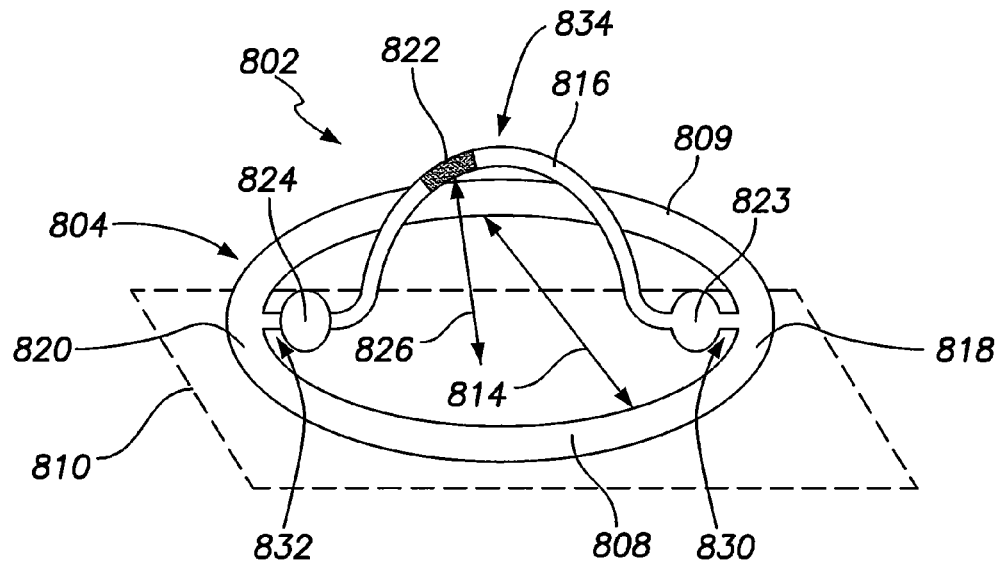
FIGS. 8A and 8B illustrate exemplary electrode assembly that may be implemented in accordance with embodiments of the present invention.
Figure 8B:
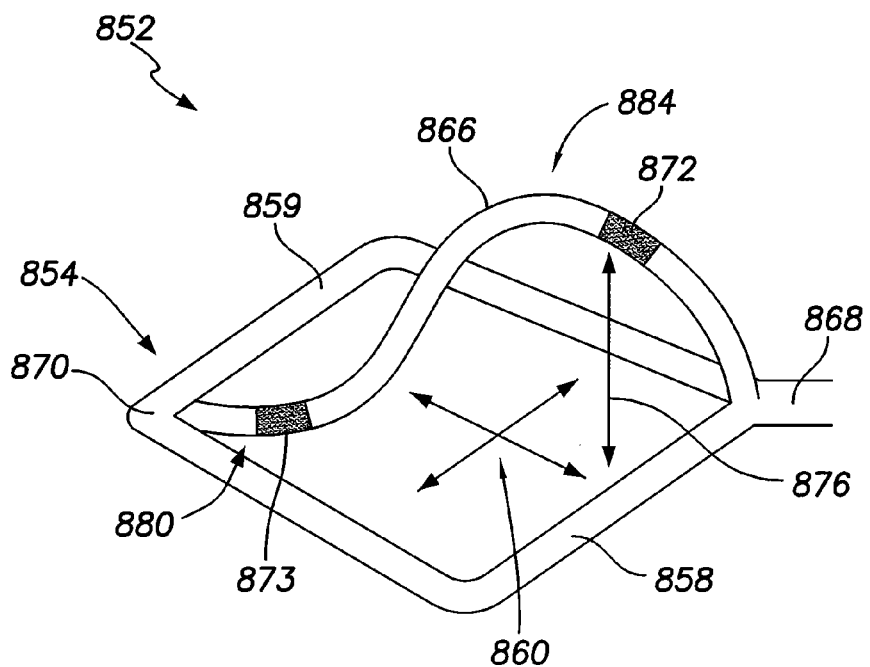

FIGS. 8A and 8B illustrate exemplary electrode assembly that may be implemented in accordance with embodiments of the present invention. FIG. 8A illustrates an electrode assembly 802 that may be provided on a distal end portion of a lead (e.g., distal end portion 306 on device 300). Optionally, the electrode assembly 802 may be provided on both ends of the lead, and/or at any desired location along the intermediate portion of the lead (e.g., anywhere along intermediate portions 308 of device 300). The electrode assembly 802 includes a frame 804 that is generally circular or oval and is generally configured to be positioned in a base plane 810. The frame 804 has one or more opposed legs 808 and 809 that are compressible. The legs are joined at proximal and distal ends 818 and 820. In the example of FIG. 8A, two legs are illustrated, but it is appreciated that one leg or more than two legs may be used. The leg 808 and 809 are formed from a biocompatible material, as discussed herein. The frame 804 is compressible with the legs 808 and 809 collapsing against one another to facilitate implant. The frame 804 may be formed to have a predetermined degree of shape memory such that once the frame 804 is no longer compressed the legs 808 and 809 return to their natural shape, such as shown in FIG. 8A. When in their natural shape, the legs 808 and 809 are separate from one another in a lateral direction by a distance 814 to define the base plane 810. The legs 808 and 809 rest against a region in the pericardial sac where the lead is positioned.

The lead assembly 802 includes at least one arm 816 that extends between the proximal and distal ends 818 and 820. The arm 816 has electrodes 822-824 distributed along the length thereof. The arm 816 is curved or bent to extend between the proximal and distal ends 818 and 820 along a non-linear "out-of-plane" path. The arm 816 extends upward, downward or in any other direction out of the base plane 810. The electrodes 822-824 are positioned along the arm 816 in a non-planar relation with respect to one another. In the example of FIG. 8A, electrodes 823 and 824 are located near opposed footer portions 830 and 832 of the arm 816 near where the arm 816 joins the frame 804. The electrode 822 is located along an intermediate raised portion 834 of the arm 816 such that the electrode 822 is positioned out of the base plane 810 by a distance 826. Optionally, one or both of the electrodes 823 and 824 may be within the base plane 810. More electrodes 822 may be positioned along the intermediate portion 834.

FIG. 8B illustrates an electrode assembly 852 that may be provided on a distal end portion of a lead (e.g., distal end portion 306 on device 300). The electrode assembly 852 includes a frame 854 that is generally square or rectangular and configured to be positioned in a base plane (defined by cross-arrows 860). The frame 854 has a pair of opposed V-shaped legs 858 and 859 that are compressible and joined at proximal and distal ends 868 and 870. One leg or more than two legs may be used. When in their natural shape, the legs 858 and 859 are separate from one another. The legs 858 and 859 rest against a region in the pericardial sac where the lead is positioned.

The lead assembly 852 includes at least one arm 866 that extends between the proximal and distal ends 868 and 870. The arm 866 has electrodes 872-873 distributed along the length thereof. The arm 866 is shaped in a wave as extending between the proximal and distal ends 868 and 870 along a non-linear "out-of-plane" path. The arm 866 extends upward, downward or in any other direction out of the base plane defined by arrows 860. The electrodes 872-873 are positioned along the arm 866 in a non-planar relation with respect to one another. The electrode 873 is located near a footer portion 880 of the arm 866 near where the arm 866 joins the frame 854. The electrode 872 is located along an intermediate raised portion 884 of the arm 866 out of the base plane 810 by a distance 876. More electrodes 872 may be positioned along the intermediate portion 884. The electrodes 822-824 and 872-873 may be used to perform bipolar sensing and are arranged non-planar with one another.

Optionally, three electrodes may be arranged to pick a vector in two dimensions. For example, three electrodes may be located along a circular ring with angles of 0, 90, 180 degrees.

Optionally, the lead may be integrated with a conventional ICD system, which performs bipolar sensing through RV and RA leads. When an intra-pericardial lead is used in combination with a conventional ICD system the intra-pericardial lead does not need to perform bipolar sensing.

In accordance with embodiments described herein, the lead is compatible with MRI systems. The leads described herein avoid antennas or conducting loops that are susceptible to MRI fields. The leads described herein may be around 5 cm in length or up to 10 to 20 cm in length. With these shorter lengths, the risks of RF heating and cardiac stimulation may be greatly reduced.

In accordance with embodiments described herein, when the lead is provided with electronics, battery and energy storage units therein for pacing/cardioversion, the lead does not experience significant forces or torque applied thereto.

The telemetry conductor 320 may receive RF energy from an external programmer/Handheld wireless control devices. The RF energy may represent wireless communications and/or power to recharge the battery in the lead. The handheld device may be a traditional programmer or may be a small portable device such as IPOD-like device. The external device will serve as a control unit that can upload data and store them in it daily as well as program pacing/sensing parameters, pacing modes and device check-ups. This handheld device provides also transferring data to remote systems or patient home care systems etc. It can have display screen for viewing signals and results. In the normal operation, the handheld "Programmer" can be kept within certain distance (<3 meters; such as in the pocket as carrying on a cellular phone).

The programmer may be used to check battery life and to recharge the battery by conveying battery power over the RF signal.

Alternatively, instead of using a single external coil/WANDA, to enhance coupling to external coils, two or more external coils/WANDA may be used by placing one on the chest and another on the back. The design of the telemetry system ensures that the current flowing in coil groups generates magnetic fields in phase (e.g., enhanced B fields near the location of intra-pericardial coils).

Figure 9:
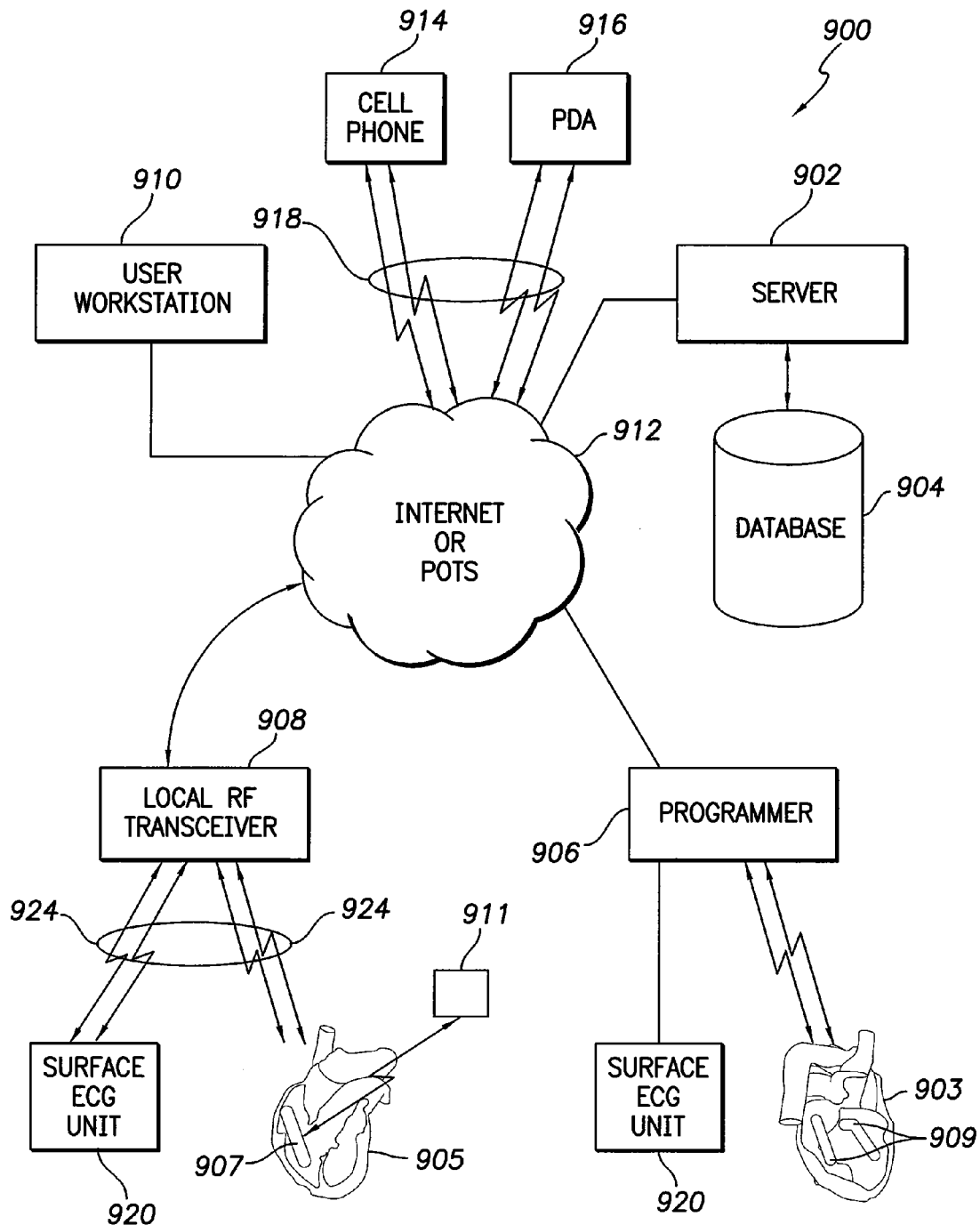
FIG. 9 illustrates a system that may be utilized in connection with the leads described herein in accordance with an embodiment.

FIG. 9 illustrates a system 900 that may be utilized in connection with the leads described herein in accordance with an embodiment. The system 900 includes a server 902 connected to a database 904, a programmer 906, a local RF transceiver 908 and a user workstation 910 electrically connected to a communication system 912. The communication system 912 may be the internet, a voice over IP (VoIP) gateway, a local plain old telephone service (POTS) such as a public switched telephone network (PSTN), a cellular phone based network, and the like. Alternatively, the communication system 912 may be a local area network (LAN), a campus area network (CAN), a metropolitan area network (MAN), or a wide area network (WAM). The communication system 912 serves to provide a network that facilitates the transfer/receipt of information.

The system 900 includes intra-pericardial medical devices 907 and 909 implemented in accordance with embodiments discussed above to include telemetry conductors, a battery, a control block and an energy storage unit. The IPMD 907 is located in the pericardial sac near a heart 905, while IPMD 909 is located in the pericardial sac near a heart 903. The IPMD 907 wireless communicates with an implanted medical device 911 (e.g., pacemaker, ICD, etc.). The IPMD 909 wirelessly communicates with an external programmer 906.

The server 902 is a computer system that provides services to other computing systems over a computer network. The server 902 interfaces with the communication system 912 to transfer information between the programmer 906, the local RF transceiver 908, the user workstation 910 as well as a cell phone 914, and a personal data assistant (PDA) 916 to the database 904 for storage/retrieval of records of information. On the other hand, the server 902 may upload raw cardiac signals from a surface ECG unit 920 or the IMD 911 via the local RF transceiver 908 or the programmer 906.

The database 904 stores information such as the measurements for the cardiogenic impedance parameters, the electrophysiologic response parameters, and the like, for a single or multiple patients. The information is downloaded into the database 904 via the server 902 or, alternatively, the information is uploaded to the server from the database 904. The programmer 906 may reside in a patient's home, a hospital, or a physician's office. Programmer 906 interfaces with the surface ECG unit 920 and the IMD 10. The programmer 906 may wirelessly communicate with the IMD 10 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 906 to the IMD 10. The programmer 906 is able to acquire cardiac signals from the surface of a person (e.g., ECGs), intra-cardiac electrogram (e.g., IEGM) signals from the IMD 10, and/or values of cardiogenic impedance parameters and electrophysiologic response parameters from the IMD 10. The programmer 906 interfaces with the communication system 912, either via the internet or via POTS, to upload the information acquired from the surface ECG unit 920 or the IMD 10 to the server 902.

The local RF transceiver 908 interfaces with the communication system 912, via a communication link 924, to upload data acquired from the surface ECG unit 920 and/or from the leads 907 and 909 and/or from the IMD 911 to the server 902. In one embodiment, the surface ECG unit 920 and the IMD 911 have a bi-directional connection with the local RF transceiver via a wireless connection. The local RF transceiver 908 is able to acquire cardiac signals from the surface of a person, intra-cardiac electrogram signals from the leads 907, 909 and the IMD 911. On the other hand, the local RF transceiver 908 may download stored data, parameters, cardiac data, and the like, from the database 904 to the leads 907, 909, the surface ECG unit 90 or the IMD 911.

The user workstation 910 may interface with the communication system 912 via the internet or POTS to download values of the cardiogenic impedance parameters and electrophysiologic response parameters via the server 902 from the database 904. Alternatively, the user workstation 910 may download raw data from the surface ECG unit 920 or IMD 10 via either the programmer 906 or the local RF transceiver 908. Once the user workstation 910 has downloaded the cardiogenic impedance parameters and electrophysiologic response parameters, the user workstation 910 may process the information in accordance with one or more of the operations described above in connection with the process 900 (shown in FIG. 9). The user workstation 910 may download the information and notifications to the cell phone 916, the PDA 918, the local RF transceiver 908, the programmer 906, or to the server 902 to be stored on the database 904. For example, the user workstation 910 may communicate an identified potential cause of pulmonary edema to the cell phone 916 of a patient or physician.

Figure 10:
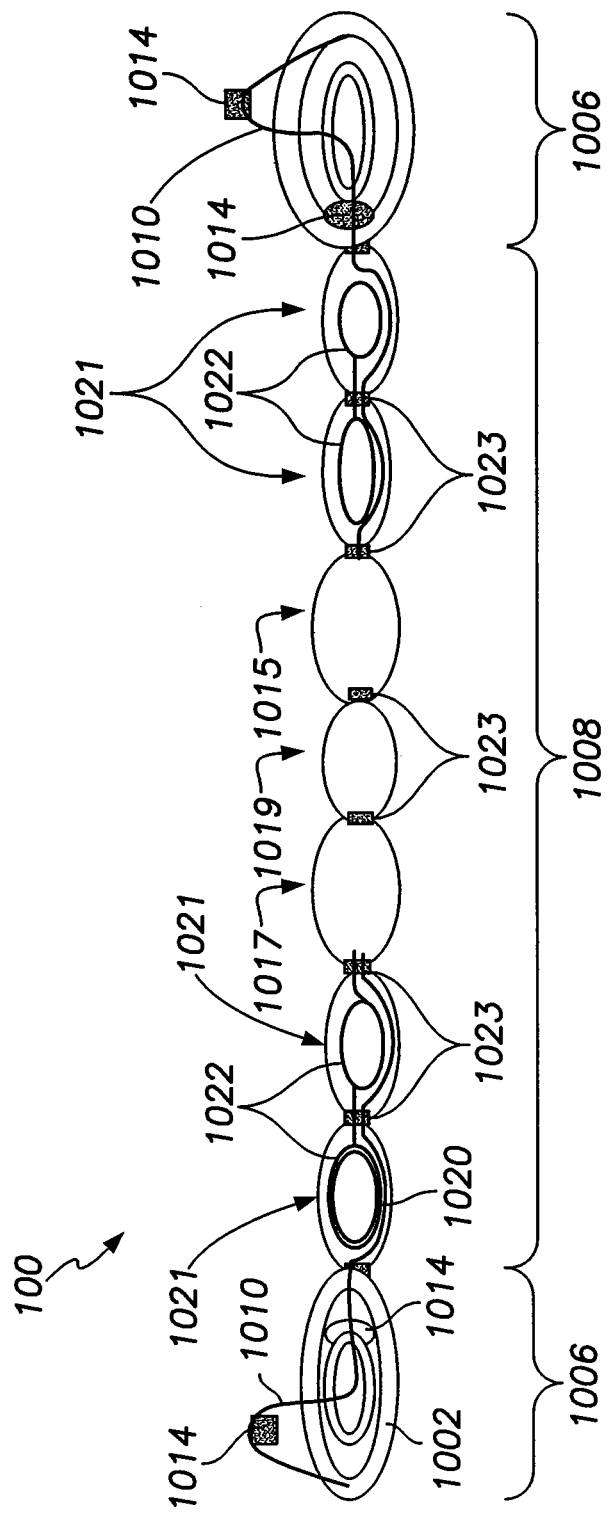
FIG. 10 illustrates an intra-pericardia medical device formed in accordance with an embodiment.

FIG. 10 illustrates an intra-pericardia (IP) device 1000 formed in accordance with an embodiment of the present invention. The device 1000 comprises a lead body 1002 having a proximal portion, a distal end portion 1006, and an intermediate portion 1008 extending between the proximal portion 1004 and the distal end portion 1006. The lead body 1002 includes a series of loop segments 321 that have openings 319 through center regions of each loop segment 321 (e.g., similar to a donut). The device 1000 includes one or more sensing and/or stimulus conductor 1010 extending along the lead body 1002. Optionally, the device 1000 may include one or more screws or helix to secure the lead body 1002 to the myocardium for fixation and as a pacing/sensing lead.

The conductor 1010 may be used to deliver lower energy or high energy stimulus, such as pacing pulses, cardioverter pulse trains, defibrillation shocks and the like. The conductor 1010 may also be used to sense electrical activity, such as physiologic and pathologic behavior and events. Terminals are joined to the stimulus and telemetry conducts 1010 and 1020, respectively, near the proximal portion 1004 of the lead body 1002. The terminal is configured to be joined to an energy source, such as an IMD. The terminal receives stimulus pulse(s) from the IMD. One or more electrodes 1014 are joined to the conduct 1010. The electrode(s) 1014 may be located near the distal end portion 1006 and/or at various positions along the intermediate portion 1008. The electrode 1014 is configured to deliver high or low energy stimulus pulses to the myocardium. The electrode 1014 may be also used to sense electrical activity of the myocardium.

A telemetry conductor 1020 is provided within the lead body 1002 and positioned to extend from the proximal portion 1004 and along the intermediate portion 1008 of the lead body 1002. The telemetry conductor 1020 is wound into a series of coil groups 1022 to form inductive loops. The coil groups 1022 operate to receive and/or transmit radio frequency (RF) energy. The telemetry conductor 1020 may be wound in a manner to receive and transmit RF energy that represents communications signals to and from an external programming device. Alternatively, or in addition, the telemetry conductor 1020 may also be wound in a manner to receive RF energy that represents power which is then used to charge an implantable medical device joined to the proximal portion 1004 of the lead body 1002. The terminal receives signals (e.g., power or data) induced into the telemetry conductor 1020 by RF energy passing about the coil groups 1022. The coil groups 1022 include at least one partial winding of the telemetry conductor 1020. Optionally, at least one of the coil groups 1022 may includes multiple windings that are at least partially spatially overlapped with one another. The coil groups 1022 are distributed along the intermediate portion 1008 and positioned to be centered along a longitudinal axis.

FIG. 10 illustrates an intra-pericardia (IP) device 1000 formed in accordance with an embodiment of the present invention. The device 1000 is configured to deliver high energy shocks to a patient such as in a cardioverter and/or defibrillator. The device 1000 comprises a lead body 1002 having distal end portions 1006, and an intermediate portion 1008 extending between the distal end portions 1006. The lead body 1002 includes a series of loop segments 321 that have closed center regions. The device 1000 includes one or more sensing and/or stimulus conductors 1010 extending along the lead body 1002. Optionally, the device 1000 may include one or more screws or helix to secure the lead body 1002 to the myocardium for fixation and as a pacing/sensing lead.

The conductor 1010 may be used to deliver high energy stimulus, such as cardioverter pulse trains, defibrillation shocks and the like. The conductor 1010 may also be used to sense electrical activity, such as physiologic and pathologic behavior and events. The lead body 1002 includes component segments 1015, 1017 and 1019, one or more of which include an energy source (e.g., one or more battery), energy storage devices (e.g., capacitors), and control electronics. For example, component segment 1015 may include the batteries, component segment 1017 may include the capacitors and component segment 1019 may include the control electronics.

The energy source, energy storage devices and control electronics may be packaged in separate component segments 1015, 1017 and 1019, respectively. The control electronics may resemble control block 350 (FIG. 3C) when configured to perform cardioversion or defibrillation functionality. Optionally, multiple component segments 1015, 1017 and 1019 may include batteries and capacitors. For example, component segment 1015 and 1017 may each include a battery and a capacitor. More than three component segments may be included. Optionally, the component segments 1015, 1017 and 1019 may be distributed apart from one another along the lead body 1002.

The loop segments 1021 and the component segments 1015, 1017 and 1019 may be formed from a common integral housing. Optionally, the loop segments 1021 and the component segments 1015, 1017 and 1019 may be formed separate from one another and joined with connectors 1023.

One or more electrodes 1014 are joined to the conduct 1010. The electrode(s) 1014 may be located near the distal end portion 1006 and/or at various positions along the intermediate portion 1008. The electrodes 1014 are configured to deliver high energy stimulus pulses to the myocardium. The electrodes 1014 may be also used to sense electrical activity of the myocardium.

A telemetry conductor 1020 is provided within the lead body 1002 and positioned to extend along the intermediate portion 1008 of the lead body 1002. The telemetry conductor 1020 is wound into a series of coil groups 1022 to form inductive loops. The coil groups 1022 operate to receive and/or transmit radio frequency (RF) energy. The telemetry conductor 1020 may be wound in a manner to receive and transmit RF energy that represents communications signals to and from an external programming device. Alternatively, or in addition, the telemetry conductor 1020 may also be wound in a manner to receive RF energy that represents power which is then used to charge an implantable medical device joined to the proximal portion 1004 of the lead body 1002. The terminal receives signals (e.g., power or data) induced into the telemetry conductor 1020 by RF energy passing about the coil groups 1022. The coil groups 1022 include at least one partial winding of the telemetry conductor 1020. Optionally, at least one of the coil groups 1022 may includes multiple windings that are at least partially spatially overlapped with one another. The coil groups 1022 are distributed along the intermediate portion 1008 and positioned to be centered along a longitudinal axis.

Figure 11:
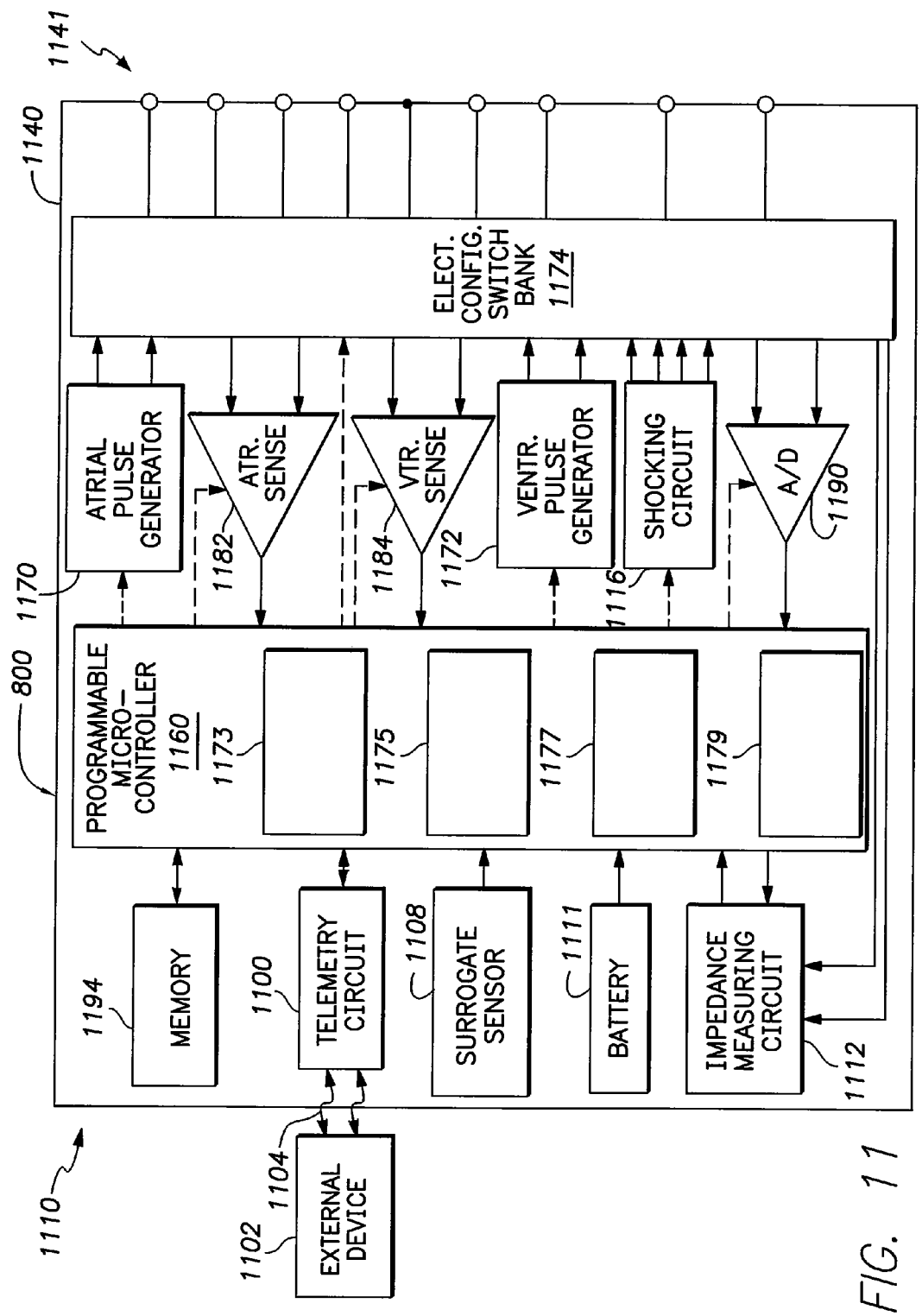
FIG. 11 illustrates a block diagram of the IPMD of FIG. 10.

FIG. 11 illustrates a block diagram of the IPMD 1110, which is capable of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 1140 for the stimulation IPMD 1110 is often referred to as the "can", "case" or "case electrode" and may be programmably selected to act as the return electrode for some or all sensing modes. The housing 1140 may further be used as a return electrode alone or in combination with one or more of the other electrodes. The housing 1140 further includes a connector (not shown) having a plurality of terminals 1141. To achieve sensing, pacing and shocking in desired chambers of the heart, the terminals 1141 are selectively connected to corresponding combinations of electrodes.

The IPMD 1110 includes a programmable microcontroller 1160 that controls the various modes of sensing and stimulation therapy. The microcontroller 1160 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 1160 includes the ability to process or monitor input signals (data) as controlled by a program code stored in memory. The details of the design and operation of the microcontroller 1160 are not critical to the present invention. Rather, any suitable microcontroller 1160 may be used. The microcontroller 1160 analyzes sensed signals and determines when an arrhythmia (e.g., fibrillation) is occurring. The microcontroller 1160 detects arrhythmias, such as ventricular tachycardia (VT), bradycardia and ventricular fibrillation (VF). The microcontroller 1160 may perform morphology detection to analyze the morphology of the cardiac signal, including detecting R wave peaks and/or detecting T wave features of interest, such as onset, peak, etc.

An atrial pulse generator 1170 and a ventricular pulse generator 1172 generate pacing and ATP stimulation pulses for delivery by desired electrodes. The electrode configuration switch 1174 (also referred to as switch bank) controls which terminals 1141 receive impedance measurement, electrical signals, shocks or pacing pulses. The pulse generators 1170 and 1172 are controlled by the microcontroller 1160 via appropriate control signals respectively, to trigger or inhibit stimulation pulses. The microcontroller 1160 controls the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

A ventricular sensing circuit 1184 may amplify, filter, digitize and/or otherwise process the sensed cardiac signals from the electrodes located in the pericardial sac proximate the RV and/or LV. The circuit 1184 may provide separate, combined or difference signals to the microcontroller 1160 representative of the sensed signals from the RV and/or LV electrodes. An atrial sensing circuit 1182 is connected through the switch 1174 to desired RA and/or LA electrodes to sense RA and/or LA cardiac activity. The switch 1174 also connects various combinations of the electrodes to an impedance measurement circuit 1112.

An impedance measuring circuit 1112 collects impedance measurements between corresponding combinations of electrodes. For example, the impedance measuring circuit 1112 may collect measured impedance for each or a subset of the sensing vectors. The impedance measurements are taken along one or more vectors through the heart over a period of time. The impedance measurements are supplied to the controller 1160.

Atrial sensing circuits 1182 and ventricular sensing circuits 1184 may also be selectively coupled to RA, LA, RV and LV electrodes for detecting the presence of cardiac activity in each of the four chambers of the heart. The switch 1174 determines the "sensing polarity" of the cardiac signal by selectively closing the appropriate switches. The outputs of the atrial and ventricular sensing circuits 1182 and 1184 are connected to the microcontroller 1160 which, in turn, is able to trigger or inhibit the atrial and ventricular pulse generators 1170 and 1172, respectively. The sensing circuits 1182 and 1184, in turn, receive control signals over signal lines from the microcontroller 1160 for purposes of controlling the gain, threshold, the polarization charge removal circuitry (not shown), and the timing of any blocking circuitry (not shown) coupled to the inputs of the sensing circuits 1182.

Cardiac signals are also applied to the inputs of an analog-to-digital (A/D) data acquisition system 1190. The data acquisition system 1190 is configured to acquire intracardiac electrogram signals, convert the raw analog data into a digital signal, and store the digital signals for later processing and/or telemetric transmission to an external device 1102. The data acquisition system 1190 samples cardiac signals across any pair of desired electrodes. The microcontroller 1160 further controls a shocking circuit 1116 by way of a control signal. The shocking circuit 1116 generates stimulating pulses of low (up to 0.5 Joules), moderate (0.5-10 Joules), or high energy (11 to 40 Joules), as controlled by the microcontroller 1160. Stimulating pulses are applied to the patient's heart through at least two shocking electrodes.

The microcontroller 1160 is further coupled to a memory 1194 by a suitable data/address bus. The memory 1194 stores programmable operating, impedance measurements, impedance derivation and therapy-related parameters used by the microcontroller 1160. The operating and therapy-related parameters define, for example, surrogate signals, contractility estimates, models, length force curves, correction factors, trend values, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 1194 through a telemetry circuit 1100 in telemetric communication with the external device 1102, such as a programmer, trans-telephonic transceiver, or a diagnostic system analyzer. The telemetry circuit 1100 is activated by the microcontroller 1160. The telemetry circuit 1100 advantageously allows intracardiac electrograms, CI measurements, surrogate signals, contractility estimates, correction factors, models, trend values and status information relating to the operation of the IPMD 1110 to be sent to and from the external device 1102 through an established communication link 1104.

The IPMD 10 may include one or more surrogate sensors 1108. The surrogate sensor(s) 1108 produces surrogate signals representative of estimates for at least one of cardiac volume and pressure of the heart when the impedance measurements were taken. For example, the surrogate sensor 1108 may sense estimates of end diastolic volume, blood pressure, heart rate, stroke volume, patient activity, respiration rate and the like. Optionally, the surrogate sensor 1108 may produce surrogate signals by identifying features of interest form the impedance measurements. For example, the sensor 1108 may collect and filter impedance signals along one or more impedance sensing vectors. The sensor 1108 may include a low-pass, band pass and/or high pass filter to filter the impedance measurements and produce non-contractility information.

The sensors 1108 may include one or more of an accelerometer, a pressure sensor, a heart sound sensor, a pulse oximetry sensor, a flow sensor and the like. While a sensor 1108 is shown within the housing of the IPMD 1110, optionally, one or more sensors 1108 may be located outside the IPMD and coupled to the IPMD 1110 through a connector. The sensor 1108 may detect a level of or changes in cardiac output, a level of changes in the physiological condition of the heart, or a level of or changes in activity (e.g., detecting sleep and wake states). The battery 1111 provides operating power to all of the circuits shown.

The controller 1160 includes, among other things, various modules to perform select types of analysis. For example, module 1173 may represent an arrhythmia detection module that analyzes sensed signals and identifies various types of arrhythmias. Module 1175 may be an ST segment analysis module that analyzes various characteristics of ST segments over multiple cardiac cycles to identify changes or patterns that are indicative of certain conditions of interest. Module 1177 may represent an ischemia detection module that analyzes sensed signals to identify different types of ischemia. Module 1179 may represent an impedance analysis module to analyze impedance measurements and, based thereon, derive estimates of cardiac output and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An intra-pericardial medical device (IPMD) comprising:
    a lead body having a proximal portion, a distal end portion, and an intermediate portion extending along a longitudinal axis between the proximal portion and the distal end portions;
    control logic connected to the intermediate portion of the lead body;
    an energy source connected to the lead body and electrically connected to the control logic;
    a stimulus conductor extending along the lead body and electrically connected to the control logic;
    an electrode provided on the lead body and electrically connected to the stimulus conductor, the electrode configured to deliver stimulus pulses; and
    a telemetry conductor provided within the lead body and positioned along the intermediate portion of the lead body, the telemetry conductor wound into a series of coil groups to form a plurality of annular, interconnected inductive loops for at least one of receiving or transmitting radio frequency (RF) energy that represents at least one of recharge power or communications signals, wherein at least two of the coil groups includes a number of coil windings wound about a lateral axis of the intermediate portion and stacked co-axially above one another along the lateral axis, the lateral axis extending in a direction transverse to the longitudinal axis of the intermediate portion, the coil groups being connected to one another in series and be distributed apart from one another within and along the lead body forming the plurality of annular interconnected inductive loops.

2. The IPMD of claim 1, wherein the intermediate portion includes series of loop segments distributed along the longitudinal axis, the loop segments having opposed sides aligned in a common plane, the loop segments having a perimeter that is flared in a lateral direction with respect to the longitudinal axis of the lead body, each of the loop segments including at least one of the coil groups.

3. The IPMD of claim 1, wherein the intermediate portion of the lead body includes a series of flared segments joined by linking regions, each of the flared segments having a pair of opposed sides separated by a thickness of the flared segment, each of the flared segments including at least one of the coil groups.

4. The IPMD of claim 1, wherein the at least one coil group includes first and second coil groups wound about different first and second lateral axes such that the first and second groups are aligned parallel to different first and second planes.

5. The IPMD of claim 1, wherein the telemetry conductor is wound in a manner to receive and transmit RF energy that represents communications signals to and from an external programming device.

6. The IPMD of claim 1, wherein the telemetry conductor is wound in a manner to receive RF energy that represents power to charge an implantable medical device joined to the proximal portion of the lead body.

7. The IPMD of claim 1, wherein each of the coil groups includes a series of windings connected in series and distributed along the intermediate portion of the lead body.

8. The IPMD of claim 1, wherein each of the coil groups includes at least one winding of the telemetry conductor.

9. The IPMD of claim 1, wherein at least one of the coil groups includes multiple windings that are at least partially spatially overlapped with one another.

10. The IPMD of claim 1, wherein the intermediate portion of the lead body extends along a longitudinal axis, the coil groups distributed along the intermediate portion and positioned to be centered upon the longitudinal axis.

11. The IPMD of claim 1, wherein the distal end portion represents a precurved distal end portion that has a distal end and a proximal end; a flexible loop member carried by the distal end portion and having a proximal segment attached to the proximal end of the distal end portion and a distal segment attached to the distal end of the distal end portion, wherein the loop member has a normally expanded state in which side portions of the loop member are spaced from the precurved distal end portion, and is adapted to assume a contracted state in response to the precurved distal end portion assuming a straightened configuration, the electrode carried by the precurved distal end portion.

12. A method to provide an intra-pericardial medical device (IPMD), comprising:
   providing a lead body having a proximal portion, a distal end portion, and an intermediate portion extending along a longitudinal axis between the proximal portion and the distal end portions;
   extending a stimulus conductor along the lead body;
   joining an electrode to the stimulus conduct near the distal end portion, the electrode configured to deliver stimulus pulses;
   extending a telemetry conductor within the lead body from the proximal portion and along the intermediate portion of the lead body; and
   winding the telemetry conductor into a series of coil groups to form a plurality of annular, interconnected inductive loops for at least one of receiving or transmitting radio frequency (RF) energy that represents at least one of recharge power or communications signals, wherein at least two of the coil groups includes a number of coil windings wound about a lateral axis of the intermediate portion and stacked co-axially above one another along the lateral axis, the lateral axis extending in a direction transverse to the longitudinal axis of the intermediate portion, the coil groups being connected to one another in series and be distributed apart from one another within and along the lead body forming the plurality of annular interconnected conductive loops.

13. The method of claim 12, wherein the intermediate portion includes a series of loop segments distributed along the longitudinal axis, the loop segments having opposed sides aligned in a common plane, the loop segments having a perimeter that is flared in a lateral direction with respect to the longitudinal axis of the lead body, each of the loop segments including at least one of the coil groups.

14. The method of claim 12, wherein the intermediate portion of the lead body includes a series of flared segments joined by linking regions, each of the flared segments having a pair of opposed sides separated by a thickness of the flared segment, each of the flared segments including at least one of the coil groups.

15. The method of claim 12, wherein the intermediate portion of the lead body includes a series of disc-shaped segments configured to lie in a common plane, each of the disc-shaped segments including one of the coil groups enclosed within an insulated shell.

16. The method of claim 12, further comprising transmitting RF energy to the telemetry conductor, the RF energy representing communications signals from an external programming device.

17. The method of claim 12, further comprising transmitting RF energy to the telemetry conductor, the RF energy representing power; and utilizing the RF energy to charge a battery within the lead.

18. The method of claim 12, further comprising providing, in the coil groups, a series of windings connected in series and distributed along the intermediate portion of the lead body.

19. The method of claim 12, wherein the at least one coil group includes first and second coil groups wound about different first and second lateral axes such that the first and second groups are aligned parallel to different first and second planes.

* * * * *